United States Patent
Lider et al.

(10) Patent No.: US 6,906,170 B1
(45) Date of Patent: Jun. 14, 2005

(54) ANTI-INFLAMMATORY PEPTIDES DERIVED FROM IL-2 AND ANALOGUES THEREOF

(75) Inventors: Ofer Lider, Kfar Bilu Bet (IL); Amiram Ariel, Rehovot (IL); Rami Hershkoviz, Herzliya (IL); Eran J. Yavin, Rehovot (IL); Matityahu Fridkin, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/763,293
(22) PCT Filed: Aug. 19, 1999
(86) PCT No.: PCT/IL99/00448
§ 371 (c)(1), (2), (4) Date: May 17, 2001
(87) PCT Pub. No.: WO00/11028
PCT Pub. Date: Mar. 2, 2000

(30) Foreign Application Priority Data

Aug. 21, 1998 (GB) .............................................. 9818370
Aug. 31, 1998 (IL) ................................................ 126009
May 16, 1999 (IL) ................................................ 129980

(51) Int. Cl.⁷ ........................ A61K 38/08; A61K 38/20; C07K 7/00; C07K 14/52
(52) U.S. Cl. ...................... 530/328; 530/300; 530/317; 530/351; 514/2; 424/85.2
(58) Field of Search ................................ 530/328, 300, 530/317, 351; 514/2; 424/85.2

(56) References Cited

FOREIGN PATENT DOCUMENTS

WO    WO 95 00538 A    1/1995

OTHER PUBLICATIONS

Fehali et al. Frontiers in Bioscience, vol. 2, pp. d12–d26, 1997.*

Ariel, A. et al., "IL–2 Induces T Cell Adherence to Extra-cellular Matrix: Inhibition of Adherence and Migration by IL–2 Peptides Generated by Leukocyte Elastase," J. Immunol. (1998), 161–5, 2465–2472.

Suzuki, K. et al., "Localization of Chemotactic Activity and 64 kD Protein Phosphorylation of Human Polymorphonuclear Leukocytes in N–terminus of the Chemotactic Protein LUCT/IL–8," Biochem. Biophys. Res. Commun. (1989), 163(3), 1298–305.

Database WPI, Section Ch, Week 199136, Derwent Publications Ltd. London, GB. AN 1991–262316, XP002133615 & JP 03 170498 A (Teikoku Hormone MFG Co, Ltd.) Jul. 24, 1991.

Yavin et al, "Synthetic peptides derived from the sequence of human C–reactive protein inhibit the enzymatic activities of human leukocyte elastase and human leukocyte cathepsin G", *Int J Peptide Protein Res* 48:465–476 (1996).

* cited by examiner

*Primary Examiner*—Prema Mertz
*Assistant Examiner*—Fozia Hamud
(74) *Attorney, Agent, or Firm*—Browdy and Neimark, PLLC

(57) ABSTRACT

Synthetic anti-inflammatory peptides derived from the sequence of IL-2 are provided. Parent peptides of the sequences Ile-Val-Leu, Glu-Phe-Leu-Asn-Arg-Trp-Ile-Thr (SEQ ID NO:1) and Arg-Met-Leu-Thr (SEQ ID NO:2), were obtained by elastase enzymatic digestion of IL-2, synthesized and modified. The peptides are useful in conditions of acute and chronic inflammation such as in autoimmune diseases.

15 Claims, 8 Drawing Sheets

SEQUENCE LISTING

<160> NUMBER OF SEQ ID NOS: 39

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 1

Glu Phe Leu Asn Arg Trp Ile Thr
 1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 2

Arg Met Leu Thr
 1

<210> SEQ ID NO 3

```
<211> LENGTH: 7
<212> TYPE: PRT
<213> ORGANISM: Artificial Sequence
<220> FEATURE:
<223> OTHER INFORMATION: Description of Artificial Sequence: synthetic

<400> SEQUENCE: 3

Asn Ile Asn Val Ile Val Leu
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: synthetic

<400> SEQUENCE: 4

Ile Val Leu Glu Leu Lys Gly
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: synthetic

<400> SEQUENCE: 5

Asn Val Ile Val Leu
 1               5

<210> SEQ ID NO 6
<211> LENGTH: 6
<212> TYPE: PRT
<213> ORGANISM: Artificial Sequence
<220> FEATURE:
<223> OTHER INFORMATION: linear or cyclic
<220> FEATURE:
<223> OTHER INFORMATION: Description of Artificial Sequence: synthetic

<400> SEQUENCE: 6

Cys Ile Val Leu Ala Cys
 1               5

<210> SEQ ID NO 7
<211> LENGTH: 7
<212> TYPE: PRT
<213> ORGANISM: Artificial Sequence
<220> FEATURE:
<223> OTHER INFORMATION: linear or cyclic
<220> FEATURE:
<223> OTHER INFORMATION: Description of Artificial Sequence: synthetic

<400> SEQUENCE: 7

Cys Ile Val Leu Ala Ala Cys
 1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: synthetic

<400> SEQUENCE: 8

Ile Val Glu Phe Leu Asn Arg Trp Ile Thr
 1               5                  10
```

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: synthetic

<400> SEQUENCE: 9

Glu Phe Leu Asn Arg Trp Ile Thr Phe Cys
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 10

Ala Thr Ile Val Glu Phe Leu Asn Arg Trp Ile Thr
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 11

Glu Phe Leu Asn Arg Trp Ile Thr Phe Cys Gln Ser
 1               5                  10

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: synthetic

<400> SEQUENCE: 12

Leu Asn Arg Trp Ile Thr
 1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 13

Arg Trp Ile Thr
 1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 14

Glu Phe Leu Asn
 1

```
<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 15

Ala Phe Leu Asn Arg Trp Ile Thr
 1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 16

Lys Phe Leu Asn Arg Trp Ile Thr
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 17

Glu Ala Leu Asn Arg Trp Ile Thr
 1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 18

Glu Val Leu Asn Arg Trp Ile Thr
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 19

Glu Phe Ala Asn Arg Trp Ile Thr
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 20

Glu Phe Leu Ala Arg Trp Ile Thr
 1               5
```

```
<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 21

Glu Phe Leu Asn Ala Trp Ile Thr
 1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 22

Glu Phe Leu Asn Glu Trp Ile Thr
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 23

Glu Phe Leu Asn Arg Ala Ile Thr
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 24

Glu Phe Leu Asn Arg Trp Ala Thr
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 25

Glu Phe Leu Asn Arg Trp Ile Ala
 1               5

<210> SEQ ID NO 26
<211> LENGTH: 8
<212> TYPE: PRT
<213> ORGANISM: Artificial Sequence
<220> FEATURE:
<221> NAME/KEY: MOD_RES
<222> LOCATION: (8)
<223> OTHER INFORMATION: AMIDATION
<220> FEATURE:
<223> OTHER INFORMATION: Description of Artificial Sequence: synthetic

<400> SEQUENCE: 26

Glu Phe Leu Asn Arg Trp Ile Thr
```

```
                1               5

<210> SEQ ID NO 27
<211> LENGTH: 11
<212> TYPE: PRT
<213> ORGANISM: Artificial Sequence
<220> FEATURE:
<223> OTHER INFORMATION: linear or cyclic
<220> FEATURE:
<223> OTHER INFORMATION: Description of Artificial Sequence: synthetic

<400> SEQUENCE: 27

Cys Glu Phe Leu Asn Arg Trp Ile Thr Ala Cys
  1               5                  10

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 28

Ala Met Leu Thr
  1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 29

Arg Ala Leu Thr
  1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 30

Arg Met Ala Thr
  1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 31

Arg Met Leu Ala
  1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 32
```

```
Lys Met Leu Thr
  1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 33

Arg Val Leu Thr
  1

<210> SEQ ID NO 34
<211> LENGTH: 4
<212> TYPE: PRT
<213> ORGANISM: Artificial Sequence
<220> FEATURE:
<221> NAME/KEY: MOD_RES
<222> LOCATION: (4)
<223> OTHER INFORMATION: AMIDATION
<220> FEATURE:
<223> OTHER INFORMATION: Description of Artificial Sequence: synthetic

<400> SEQUENCE: 34

Arg Met Leu Thr
  1

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 35

Pro Lys Leu Thr Arg Met Leu Thr
  1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 36

Arg Met Leu Thr Phe Lys Phe Tyr
  1               5

<210> SEQ ID NO 37
<211> LENGTH: 7
<212> TYPE: PRT
<213> ORGANISM: Artificial Sequence
<220> FEATURE:
<223> OTHER INFORMATION: linear or cyclic
<220> FEATURE:
<223> OTHER INFORMATION: Description of Artificial Sequence: synthetic

<400> SEQUENCE: 37

Cys Arg Met Leu Thr Ala Cys
  1               5

<210> SEQ ID NO 38
<211> LENGTH: 4
<212> TYPE: PRT
<213> ORGANISM: Artificial Sequence
```

-continued

```
<220> FEATURE:
<223> OTHER INFORMATION: Description of Artificial Sequence: synthetic

<400> SEQUENCE: 38

Thr Leu Met Arg
  1

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: synthetic

<400> SEQUENCE: 39

Thr Ile Trp Arg Asn Leu Phe Glu
  1               5
```

ANTI-INFLAMMATORY PEPTIDES DERIVED FROM IL-2 AND ANALOGUES THEREOF

REFERENCE TO RELATED APPLICATIONS

The present application is the national stage under 35 U.S.C. 371 of international application PCT/IL99/00448, filed 19 Aug. 1999, which designated the United States, which international application was published under PCT Article 21(2) in English.

FIELD OF THE INVENTION

The present invention relates to anti-inflammatory peptides derived from pro-inflammatory IL-2, derivatives thereof, and to pharmaceutical compositions comprising said anti-inflammatory peptides.

BACKGROUND OF THE INVENTION

The migration of T cells through tissues is regulated by adhesion receptors, such as integrins, and by receptors that receive signals provided by pro-inflammatory mediators, such as cytokines, chemokines, and extracellular matrix (ECM)-degrading enzymes (Gilat et al., 1996; Butcher and Picker, 1996).

IL-2 is a 15.5 kDa glycoprotein that participates in the development of inflammation and in the regulation of apoptosis (Taniguchi and Minami, 1993). In addition to its pro-activatory and proliferative roles, IL-2 also induces neutrophil adhesion to umbilical vein endothelial cells in a CD18-mediated manner (Li et al., 1996) as well as chemotactic responses in T cells, both directly and via regulating their expression of CC chemokine receptors (Loetscher et al., 1996). The IL-2 receptor consists of three distinct membrane chains: the $\alpha$-, $\beta$- and $\gamma$-chains. Anti-IL-2 antibodies that recognize amino acid epitopes in the N-terminal region of IL-2 can inhibit IL-2-induced lymphocyte proliferation. The C-terminal portion of IL-2 and its three Cys residues seem to contribute to the folding and active conformation of IL-2 (Kuo and Robb, 1986).

The majority of neutrophil elastase (also termed human leukocyte elastase; HLE), which exists as either a membrane-bound or soluble moiety, is produced and released by neutrophils, although small amounts are also produced by macrophages, monocytes, and T cells (Packard et al., 1995). Elastase degrades basement membrane and ECM glycoproteins, such as elastin, collagen, and fibronectin (FN), as well as molecules expressed on the surface of T cells, e.g., CD4, CD8, and CD2 (Doring et al., 1995).

SUMMARY OF THE INVENTION

It has now been surprisingly observed, according to the present invention, that enzymatic degradation of IL-2 by proteolytic enzymes that participate in the breakdown of the extracellular matrix (ECM) results in small peptidic fragments that possess anti-inflammatory activity.

A first aspect of the present invention therefore relates to anti-inflammatory peptides derived from IL-2, and to anti-inflammatory derivatives of said peptides.

The anti-inflammatory peptides of the present invention are defined as such by virtue of their ability to inhibit at least one of the following processes in vitro: (a) adhesion of activated T cells to ECM proteins; (b) chemotactic migration of T cells through ECM proteins; (c) cytokine- or mitogen-induced T cell proliferation; (d) cytokine secretion by cytokine- or mitogen-stimulated T cells; (e) spontaneous or cytokine-induced secretion of a cytokine such as IL-1$\beta$ or, preferably, IL-8, from intestinal epithelial cells.

A second aspect of the present invention relates to a method for identifying anti-inflammatory peptides derived from IL-2, which comprises:

(i) carrying out enzymatic digestion of IL-2 with a proteolytic enzyme that participates in the breakdown of the extracellular matrix (ECM);

(ii) testing the fractions obtained in (i) for their in vitro ability to inhibit at least one of the following processes: (a) adhesion of activated T cells to ECM proteins; (b) chemotactic migration of T cells through ECM proteins; (c) cytokine- or mitogen-induced T cell proliferation; (d) cytokine secretion by cytokine- or mitogen-stimulated T cells; (e) spontaneous or cytokine-induced secretion of a cytokine such as IL-1$\beta$or, preferably, IL-8, from intestinal epithelial cells;

(iii) selecting the fractions of (ii) active in at least one of the bioassays (a) to (e), fractionating each fraction to isolate individual peptides thereof, and submitting each isolated peptide to sequencing and synthesis; and (iv) carrying out one or more of the bioassays (a) to (e) with a peptide isolated in step (iii), and selecting those peptides that exhibit anti-inflammatory activity in at least one of said bioassays.

The second aspect of the invention further relates to the peptides obtainable from the method of identification described above and peptide derivatives thereof.

The proteolytic enzyme is one capable of processing the glycoprotein constituents of tissues and blood vessel walls and may be elastase, a collagenase or a metalloprotease such as metalloelastase, matrix metalloprotease-2 (MMP-2) and matrix metalloprotease-9 (MMP-9). In a preferred embodiment, the proteolytic enzyme is elastase.

The anti-inflammatory synthetic peptides of the present invention have been characterized by their possession of inhibitory activity in at least one of processes (a) to (e) given above, the anti-inflammatory peptide being preferably active in at least one of assays (a), (b) or (e).

A third aspect of the invention relates to pharmaceutical compositions comprising at least one anti-inflammatory synthetic peptide of the invention and a pharmaceutically acceptable carrier. This aspect includes also the use of said peptides for the preparation of pharmaceutical compositions for the treatment and/or alleviation of acute and chronic inflammatory disorders.

A fourth aspect of the invention relates to a method for the treatment and/or alleviation of acute and chronic inflammatory disorders comprising administering to a subject in need thereof an effective amount of an anti-inflammatory synthetic peptide of the invention.

BRIEF DESCRIPTION OF THE DRAWINGS

FIG. 4A: T cell adhesion to FN in the presence of IL-2 fractions and the IL-2 peptides Ile-Val-Leu (IVL), Glu-Phe-Leu-Asn-Arg-Trp-Ile-Thr (EFLNRWIT) (SEQ ID NO:1), and Arg-Met-Leu-Thr (RMLT) (SEQ ID NO:2), herein designated pep1, pep2 and pep3, respectively. FIG. 4B. The effects on T cell adhesion to FN of the inversely synthesized IL-2 peptides Leu-Val-Ile (LVI), Thr-Leu-Met-Arg (TLMR) and Thr-Ile-Trp-Arg-Asn-Leu-Phe-Glu (TIWRNLFE) (SEQ ID NO:38). T cells were activated with IL-2 (10 U/ml) and seeded onto FN-coated wells in the presence of IL-2, fraction 2, fraction 8, or inversed IL-2 peptides. FIG. 4C. Effects of pre-treatments of T cells with the IL-2 peptides pep1, pep2 and pep3, on the subsequent IL-2-induced T cell adhesion to FN. T cells used were untreated or pre-treated with the indicated peptides (1 pg/ml; 60 min, 37° C., 10% $CO_2$, humidified atmosphere), washed twice, exposed to IL-2, and seeded onto the FN-coated wells. After 30 min at 37° C., T cell adhesion was measured. One experiment representative of five.

DETAILED DESCRIPTION OF THE INVENTION

Figure 1A:
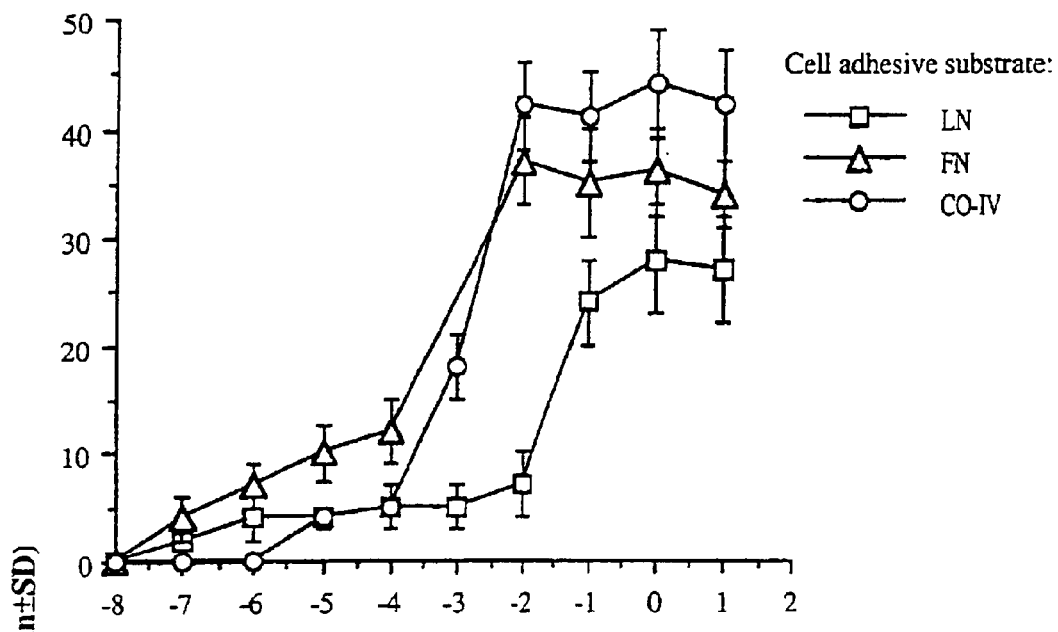
FIGS. 1A–1B show induction of T cell adhesion to fibronectin (FN), laminin (LN), collagen type IV (CO-IV) (FIG. 1A) and ECM (FIG. 1B) by IL-2. [$^{51}$Cr]-Labeled human T cells were seeded onto FN-, LN, CO-IV, and ECM-coated microtiter wells together with IL-2. After 30 min at 37° C., non-adherent T cells were removed, the adherent cells were lysed, and the percentage of T cells that had adhered was determined. One experiment representative of four.

IL-2 and elastase are prominent mediators of leukocyte extravasation and migration from the vasculature through the ECM to sites of inflammation. The present invention is based on the assumption that, in contrast to the pro-adhesive effects of the intact IL-2 molecule, certain short IL-2-derived peptides, which may occur in vivo, can inhibit the interactions of T cells with ECM, and that this interference is independent of the effects of the peptides on the activation of T cells by IL-2. We also assumed that such moieties of IL-2 can prevent the arrival of T cells at inflamed sites.

An important feature of elastase is its ability to act in both soluble and immobilized forms, since a migrating immune cell that expresses immobilized elastase may encounter matrix-bound IL-2, among other cytokines. This made neutrophil elastase a likely candidate for the physiologic production of these inhibitory peptides. Indeed, it was found, according to the present invention, that the processing of recombinant IL-2 by elastase resulted in the production of at least eight different by-products.

Three of the products generated by processing of recombinant IL-2 by neutrophil elastase (present in HPLC fractions 2, 7 and 8), inhibited IL-2-mediated T cell adhesion to FN. Amino acid composition analysis and amino acid sequencing revealed that fraction 2 contained the tripeptide Ile-Val-Leu (IL-$2_{112-114}$) (herein designated pep3) and the tetrapeptide Arg-Met-Leu-Thr (IL-$2_{58-61}$) (SEQ ID NO:2) (herein designated pep3), and fraction 8 the octapeptide Glu-Phe-Leu-Asn-Arg-Trp-Ile-Thr (IL-$2_{136-143}$) (SEQ ID NO:1) (designated pep2). The pep3 appeared to be located within the IL-2-binding site of the α-chain of the IL-2R, whereas pep1 and pep2 are located at sites far from the receptor-binding sites of IL-2. These peptides, at a picomolar range of concentrations (i.e., 0.01–1 pg/ml), inhibited the IL-2, as well as MIP-1β-induced chemotaxis of human T cells through FN-coated polycarbonate membranes.

These peptides were synthesized and the synthetic peptides were shown to exhibit the same activity as the IL-2 digested fractions 2 and 8. Thus, in one preferred embodiment, the IL-2 derived peptides of the invention are the peptides:
(pep1) Ile-Val-Leu,
(pep2) Glu-Phe-Leu-Asn-Arg-Trp-Ile-Thr (SEQ ID NO:1)
(pep3) Arg-Met-Leu-Thr (SEQ ID NO:2), The chemoattractive capacity of IL-2 in T cell migration studies in vitro has been shown by using bare polycarbonate filters or collagen- or Matrigel-coated membranes as immobilized substrates. T cell migration in these systems was proved to be IL-2R β-chain-specific and depended on the activities of the matrix-degrading gelatinases (Leppert et al., 1995). According to the present invention, the IL-2 peptides pep1, pep2, pep3, in addition to their anti-migratory effects, also inhibited T cell adhesion to FN induced by various physiologic and non-physiologic stimuli. Nevertheless, none of them, at 1 to 100 pg/ml, interfered with either PHA- or IL-2-mediated proliferative responses of human T cells, nor did these peptides inhibit the secretion of TNF-α and IFN-γ from these proliferating cells (not shown). Moreover, the inversely synthesized molecules, Leu-Val-Ile, Thr-Leu-Met-Arg (SEQ ID NO:38), and Thr-Ile-Trp-Arg-Asn-Leu-Phe-Glu (SEQ ID NO:39), did not inhibit T cell adhesion to FN.

Thus, the migration- and adhesion-suppressive capabilities of pep1, pep2 and pep3 are specific, and are not due to toxic cell death.

How do the elastase-derived IL-2 peptides exert their inhibitory functions? We have demonstrated, according to the present invention, that the three peptides pep1, pep2 and pep3 do not have to be present during the entire period of the adhesion assay, since their anti-adhesive effect was apparent even after their removal from the assay prior to T cell activation with IL-2. This finding also implies that pep1, pep2 and pep3 do not function by interacting with putative cell-adhesive epitopes present on the tested ECM glycoproteins. It seems to be highly unlikely that two of these peptides (pep1 and pep2) exert their biologic functions by interacting with the IL-2R subunits or by directly binding to $\beta_1$-specific integrins. The IL-2 peptides interfered with different modes of T cell activation, leading to their adhesion to the tested matrix proteins. Moreover, both pep1 and pep2, used in a picomolar range of concentrations, appear to block T cell adhesion not only to FN, mediated predominantly via the $\alpha_4\beta_1$ and $\beta_5\beta_1$ integrins, but also to LN; T cell adhesion to LN was mediated primarily through the $\alpha_3\beta_1$ and $\beta_6\beta_1$ integrins. Interesting, however, is the fact that pep3 (Arg-Met-Leu-Thr (SEQ ID NO:2) resides within the IL-2R$\alpha$-binding site of IL-2; two residues, $Arg^{58}$ and $Phe^{62}$, which are present within and adjacent to this peptide, respectively, were shown to be critical for IL-2-IL-2R interactions. Therefore, it will also be interesting to examine whether the degradation of IL-2 by elastase produces compounds that can interfere with IL-2 binding to its receptor and with the biologic outcome of such molecular interactions.

The ability of pep2 as well as pep1 and pep3 (data not shown) to inhibit the PMA- and IL-2-induced T cell adhesion to FN is probably linked to its ability to block the reorganization of the intracellular actin cytoskeleton. Integrin-cytoskeleton associations can modulate cell adhesion to ECM ligands, cell spreading in areas of cell contact with the substratum, and the micro-clustering and redistribution of $\beta_1$ integrins on the cell surface at sites of focal adhesion located at the ends of the actin fibers (Otey et al., 1990). Similar observations were noted for T cell activation by IL-2 (and PMA) and attachment to FN. Although the intracellular mechanisms of action of the elastase-generated fractions and peptides have not yet been determined, we postulate that these proteins effect the adhesion and migration of T cells within the ECM by active inhibition of intracellular signal transduction pathways linked to cytoskeleton organization, resulting in an inhibition of micro-clustering and an association of integrins with cytoskeletal elements.

Our findings according to the present invention imply that the tissue-invading T cells themselves can dynamically regulate their own functions. Both adhesion- and migration-promoting stimuli (i.e. intact IL-2) and suppressive by-products of inflammatory mediators can be present, although not necessarily simultaneously, within the inflammatory milieu. At the early stages of inflammation, both IL-2 and elastase may function concomitantly to activate T cells to penetrate tissues. Later, the degradation peptide products of IL-2, generated by elastase, may inhibit T cell migration, inhibit the co-stimulatory effects of IL-2 and other mediators, and probably signal the termination of the inflammatory reaction.

As stated before, the invention relates to anti-inflammatory peptides derived from the IL-2 sequence and to derivatives thereof, said anti-inflammatory activity being assessed by their ability to inhibit at least one of the following processes in vitro: (a) adhesion of activated T cells to ECM proteins; (b) chemotactic migration of T cells through ECM proteins; (c) cytokine- or mitogen-induced T cell proliferation; (d) cytokine secretion by cytokine- or mitogen-stimulated. T cells; (e) spontaneous or cytokine-induced secretion of a cytokine such as IL-1$\beta$ or, preferably, IL-8, from intestinal epithelial cells.

The in vitro bioassays (a) to (e) are well-known in the art. Thus, for example, assays (a), (b) and (e) may be carried out as described in the section Materials and Methods hereinafter. Assay (c), for inhibition of cytokine- or mitogen-induced T cell proliferation, is carried out as follows: A total of $25 \times 10^5$ of human T cells in 0.2 ml of RPMI medium supplemented with 5% heat-inactivated FCS (Gibco), antibiotics, 1% Hepes buffer, 1% glutamine and $5 \times 10^{-5}$ M 2-mercaptoethanol (ME), are added per well. T cell activation is tested by adding either the cytokine IL-2 (100 U/ml) or the mitogen Con-A (2.5 $\mu$g/ml) to the culture wells in the beginning of the assay. The IL-2-derived peptides or their derivatives are added to the culture wells (different amounts, 10 microliters) for the entire period of the assay. [$^3$H]-Thymidine is added to the microtiter 96 U-form well plates 18 h before harvesting the cultures on day 3 onto glass fiber filters and counted by liquid scintillation counter. Mean CPM and SD from quadriplicate culture are then presented. Assay (d), for inhibition of cytokine secretion by cytokine- or mitogen-stimulated T cells, is carried out similar to the proliferation assay (c), except for one modification: the supernatants of activated T cells (or any other leukocytes derived from human blood), treated with the different peptides, are collected and assayed for IL-2 and TNF-$\alpha$, using conventional ELISA kits.

In vivo bioassays may also be used to determine anti-inflammatory activity of the peptides of the invention, examples of which include: (1) inhibition of experimental delayed type hypersensitivity (DTH) reactivity carried out, for example, as described in PCT Publication No. WO 94/11006, Example 5.2; (2) treatment of experimental adjuvant arthritis (AA) in rats carried out, for example, as described in PCT Publication No. WO 94/11006, Example 5.7: and (3) treatment of experimental autoimmune encephalomyelitis (EAE) in guinea pigs, a model disease for multiple sclerosis, carried out, for example, as described in U.S. Pat. No. 5,206,223.

The term "peptides of the invention" as used hereinafter includes the synthetic peptides pep1, pep2, and pep3 derived from IL-2 as well as synthetic analogues thereof, and comprise:

(i) peptides pep1, pep2, and pep3 of the sequences:
  (pep1) Ile-Val-Leu
  (pep2) Glu-Phe-Leu-Asn-Arg-Trp-Ile-Thr (SEQ ID NO:1)
  (pep3) Arg-Met-Leu-Thr (SEQ ID NO:2)
(ii) peptides obtained from pep2 by deletion of one or more amino acid residues,
(iii) peptides obtained by addition to peptides (i) or (ii) of one or more natural or non-natural amino acid residues;
(iv) peptides obtained by replacement of one or more amino acid residues of peptides (i) to (iii) by the corresponding D-stereomer, by another natural amino acid residue or by a non-natural amino acid residue;
(v) chemical derivatives of the peptides (i) to (iv);
(vi) cyclic derivatives of peptides (i) to (v);
(vii) dual peptides consisting of two of the same or different peptides (i) to (vi), wherein the peptides are covalently linked to one another directly or through a spacer; and (viii) multimers comprising a number of the same or different peptides (i) to (vi).

The term "peptide derivative" or "peptide analogue" as used throughout the specification and claims herein is intendend to include the derivatives defined in (ii) to (viii) above, namely peptides obtained by deletion, addition, or replacement of a natural amino acid residue by the corresponding D-stereomer or by a non-natural amino acid residue, chemical derivatives of the peptides, cyclic peptides, dual peptides and multimers of the peptides.

Typically, modifications are made that retain the anti-inflammatory effect of the parent peptides pep1, pep2 and pep3. Any of the above modifications may be utilized alone or in combination, provided that the modified sequence retains anti-inflammatory activity, preferably at least 30% of the anti-inflammatory activity, more preferably at least the same activity or higher, of the parent peptide, identified by means of the above described assays.

Deletion of 1–4 amino acid residues of pep2 may be made at the N- or the C-terminal such as for example peptides pep19 and pep21, respectively, in Table 1 hereinafter. Addition of one or more natural or non-natural amino acid residues may be made at the N- or the C-terminal of each of the parent peptides pep1, pep2 and pep3, such as for example peptides pep4, pep5 and pep6 (analogues of pep1), the peptides pep15 and pep17 (analogues of pep2), and the peptide pep43 (analogue of pep3).

Substitutions include replacement of the natural amino acid residues by the corresponding D-amino acid residue, for example to increase blood plasma half-life of a therapeutically administered peptide, or by different natural amino acid residues or by non-natural amino acid residues. Thus, the peptide or peptide derivative of the invention may be all-L, all-D or a D,L-peptide. Examples of non-natural amino acids include, but are not limited to, Nβ-alkyl, particularly Nβ-methyl, amino acids*, Cα-alkyl, particularly Cα-methyl, amino acids*, halo derivatives of natural amino acids such as trifluorotyrosine*, p-Cl-phenylalanine*, p-Br-phenylalanine* and p-I-phenylalanine*, β-alanine (β-Ala)*, L-α-aminobutyric acid*, L-γ-aminobutyric acid (γ-Abu)*, L-α-aminoisobutyric acid (α-Aib)*, L-ε-aminocaproic acid*, 7-aminoheptanoic acid*, L-norleucine (Nle)*, L-norvaline (Nva)*, L-p-nitro-phenylalanine*, L-hydroxyproline (Hyp)*, L-thioproline*, ornithine (Orn)$^{\#*}$, homoarginine (homoArg)#, diaminobutyric acid (Dab)$^{\#*}$, pyridylalanine*, thienylalanine*, naphthylalanine*, phenylglycine*, methyl derivatives of phenylalanine (Phe) such as L-4-methyl-Phe* and L-pentamethyl-Phe*, L-4-amino-Phe*, L-4-isopropyl-Phe*, L-4-phenyl-Phe*, L-4-benzyl-Phe*, 1,2,3,4-tetrahydroisoquinoline-3-carboxylic acid (L-Tic)*, L-methyl-Tyr*, and L-diaminopropionic acid (Dap)$^{\#*}$. The notation * has been utilised to indicate the hydrophobic nature of the moiety whereas # has been utilised to indicate the hydrophilic nature of the derivative, and #* indicates amphipathic characteristics.

A "chemical derivative" of a peptide of the invention includes, but is not limited to, a derivative containing additional chemical moieties not normally a part of the peptide provided that the derivative retains the anti-inflammatory function of the peptide. Examples of such derivatives are: (a) N-acyl derivatives of the amino terminal or of another free amino group, wherein the acyl group may be either an alkanoyl group, e.g. acetyl, hexanoyl, octanoyl, or an aroyl group, e.g. benzoyl; (b) esters of the carboxy terminal or of another free carboxy or hydroxy groups; (c) amides of the carboxy terminal or of another free carboxy groups produced by reaction with ammonia or with a suitable amine, resulting in the C-terminus or another carboxy group being in the form —C(O)—NH—R, wherein R may be hydrogen, C1–6 alkyl, such as methyl, ethyl, propyl, isopropyl, butyl, isobutyl, pentyl or hexyl, aryl such as phenyl, and aralkyl such as benzyl, such amidation being advantageous in providing additional stability and possibly enhanced activity to the peptide; (d) glycosylated derivatives; (e) phosphorylated derivatives; (f) derivatives conjugated to lipophilic moieties e.g. caproyl, lauryl, stearoyl; and (g) derivatives conjugated to an antibody or other cellular ligands. Also included among the chemical derivatives are those derivatives obtained by modification of the peptide bond —CO—NH—, for example by (a) reduction to —CH$_2$—NH—; (b) alkylation to —CO—N (alkyl)-; (c) inversion to —NH—CO—.

The term "cyclic peptides" as used herein are cyclic derivatives containing either an intramolecular disulfide bond, i.e. —S—S—, an intramolecular amide bond, i.e. —CONH— or —NHCO—, or intramolecular S-alkyl bonds, i.e. —S—(CH$_2$)$_n$—CONH— or —NH—CO(CH$_2$)$_n$—S—, wherein n is 1 or 2. The cyclic derivatives containing an intramolecular disulfide bond may be prepared by conventional solid phase synthesis while incorporating suitable S-protected cysteine or homocysteine residues at the positions selected for cyclization such as the amino and carboxy terminals of the peptides, with the option of including spacing residues, such as (Ala)$_n$, (Gly)$_n$, where n is from 1 to 4, or non-natural amino acids such as 6-aminocaproic acid, between the terminal residue and the linking residue. The linking residues may then be linked together using known techniques to form cyclicized peptide derivatives. For example, the linear peptides Cys-Ile-Val-Leu-Ala-Cys (SEQ ID NO:6), Cys-Ile-Val-Leu-Ala-Ala-Cys (SEQ ID NO:7), Cys-Arg-Met-Leu-Thr-Ala-Cys (SEQ ID NO:37) and Cys-Glu-Phe-Leu-Asn-Arg-Trp-Ile-Thr-Ala-Cys (SEQ ID NO:27) were prepared and cyclized according to methods known in the art for formation of a disulphide bond. Following completion of the chain assembly, cyclization can be performed either by selective removal of the S-protecting groups with a consequent on-support oxidation of free corresponding two SH-functions, to form S—S bonds, followed by conventional removal of the product from the support and appropriate purification procedure, or by removal of the peptide from the support along with complete side-chain deprotection, followed by oxidation of the free SH-functions in highly dilute aqueous solution. The cyclic derivatives containing an intramolecular amide bond may be prepared by conventional solid phase synthesis while incorporating suitable amino and carboxyl side-chain protected amino acid derivatives at the positions selected for cyclization. The cyclic derivatives containing intramolecular —S-alkyl bonds may be prepared by conventional solid phase synthesis while incorporating an amino acid residue with a suitable amino-protected side chain, and a suitable S-protected cysteine or homocysteine residue at the positions selected for cyclization.

A "dual peptide" according to the invention consists of two the same or different peptides or peptide derivatives of the invention covalently linked to one another directly or through a spacer such as by a short stretch of alanine residues or by a putative site for proteolysis by cathepsin (see U.S. Pat. No. 5,126,249 and European Patent No. 495,049 with respect to such sites). This will induce site-specific proteolysis of the preferred form into the two desired analogues.

"Multimers" according to the invention consist of polymer molecules formed from a number of the same or different peptides or derivatives thereof. The polymerization is carried out with a suitable polymerization agent, such as 0.1% glutaraldehyde (Audibert et al. (1981) Nature, 289:593).

Modifications to the amino acid residues in the peptides of the present invention are discussed below using nomenclature as given in the Table below:

| ALIPHATIC | Non-polar, neutral | Gly, Ala, Pro |
|---|---|---|
| Low hydrophobic | | |
| High hydrophobic | | Ile, Leu, Val, Met |
| Low hydrophilic | Polar, neutral | Cys, Ser, Thr |
| High hydrophilic | | Asn, Gln |
| Hydrophilic | Polar-negatively charged | Asp, Glu |
| | Polar-positively charged | Lys, Arg, His |
| AROMATIC | | Phe, Trp, Tyr |
| hydrophobic | | |

Thus, in one preferred embodiment, the present invention relates to the synthetic anti-inflammatory peptide Ile-Val-Leu (pep1), and to anti-inflammatory peptides resulting from the modification thereof by:

(a) elongation by up to 3–4 further amino acid residues at the N- and/or C-terminal, such as in pep11 and pep13, or preferably according to the natural sequence of IL-2;

(b) substitution of the Ile residue by a natural or non-natural amino acid hydrophilic polar neutral or negatively charged, or hydrophobic non-polar neutral amino acid residue, preferably selected from Glu, Asp, Asn, Gln, Ala, Val;

(c) substitution of the Val residue by a hydrophobic, non-charged natural or non-natural amino acid residue, preferably selected from Ala, Ile, Leu, Met, Nle, Phe;

(d) substitution of the Leu residue by a hydrophobic, non-charged natural or non-natural amino acid residue, preferably selected from Ala, Ile, Met, Nle, Phe, Val;

(e) amidation of the C-terminal Leu residue;

(f) cyclization of pep1 or of any peptide of (a) to (e); and (g) any combination of (a) to (f).

Examples of such modified peptides derived from pep1 include;

(pep4) Asn-Ile-Asn-Val-Ile-Val (SEQ ID NO:3),
(pep5) Ile-Val-Leu-Glu-Leu-Lys-Gly (SEQ ID NO:4),
(pep6) Asn-Val-Ile-Val-Leu (SEQ ID NO:5)
(pep7) Ala-Val-Leu
(pep8) Ile-Ala-Leu
(pep9) Ile-Val-Ala
(pep10) Glu-Val-Leu
(pep11, linear) and (pep12, cyclic) Cys-Ile-Val-Leu-Ala-Cys (SEQ ID NO:6) and,
(pep13, linear) and (pep14, cyclic) Cys-Ile-Val-Leu-Ala-Ala-Cys (SEQ ID NO:7).

In a further preferred embodiment, the present invention relates to the synthetic anti-inflammatory peptide Glu-Phe-Leu-Asn-Arg-Trp-Ile-Thr (pep2) (SEQ ID NO:1), and to anti-inflammatory peptides resulting from the modification thereof by;

(a) elongation by up to 4 further amino acid residues at the C and/or N-terminal ends; such as in pep34, or preferably according to the natural sequence of IL-2;

(b) substitution of the Glu residue by a natural or non-natural charged or polar charged amino acid residue, preferably selected from Lys, Arg, Asp, Gln, Asn;

(c) substitution of the Phe residue by a natural or non-natural hydrophobic aliphatic or aromatic amino acid residue, preferably selected from Ala, Val, Ile, Leu, Tyr, Trp, Phe, Met, Nle;

(d) substitution of the Leu residue by a natural or non-natural hydrophobic aliphatic or aromatic amino acid residue, preferably selected from Ala, Val, Ile, Leu, Tyr, Trp, Phe, Met, Nle;

(e) substitution of the important Asn residue by a hydrophilic, non-charged, aliphatic natural or non-natural amino acid residue such as Gln;

(f) substitution of the Arg residue by a positively charged, natural or non-natural amino acid residue, preferably selected from Lys, Orn, homoArg, (g) substitution of the Trp residue by a natural or non-natural hydrophobic, aliphatic or aromatic, amino acid residue, preferably selected from Tyr, Ile, Leu, Nle, Tic, Phe, 4-phenyl-Phe, 4-methyl-Phe;

(h) substitution of the Ile residue by a natural or non-natural hydrophobic, aliphatic or aromatic, amino acid residue, preferably selected from Tyr, Phe, Leu, Nle, Tic;

(i) substitution of the Thr residue by an aliphatic hydrophobic amino acid residue such as Ala, Ile, Leu, or a hydroxy- or thio-containing amino acid residue preferably selected from Cys, Ser;

(j) truncation by up to 4 amino acid residues from either the C or N terminal;

(k) amidation of the C-terminal Thr;

(l) cyclization of pep2 or of any peptide of (a) to (k); and (m) any combination of (a) to (l).

Examples of such modified peptides derived from pep2 include:

(pep15) Ile-Val-Glu-Phe-Leu-Asn-Arg-Trp-Ile-Thr (SEQ ID NO:8)
(pep16) Glu-Phe-Leu-Asn-Arg-Trp-Ile-Thr-Phe-Cys (SEQ ID NO:9)
(pep17) Ala-Thr-Ile-Val-Glu-Phe-Leu-Asn-Arg-Trp-Ile-Thr (SEQ ID NO:10)
(pep18) Glu-Phe-Leu-Asn-Arg-Trp-Ile-Thr-Phe-Cys-Gln-Ser (SEQ ID NO:11)
(pep19) Leu-Asn-Arg-Trp-Ile-Thr (SEQ ID NO:12)
(pep20) Arg-Trp-Ile-Thr (SEQ ID NO:13)
(pep21) Glu-Phe-Leu-Asn (SEQ ID NO:14)
(pep22) Ala-Phe-Leu-Asn-Arg-Trp-Ile-Thr (SEQ ID NO:15)
(pep23) Lys-Phe-Leu-Asn-Arg-Trp-Ile-Thr (SEQ ID NO:16)
(pep24) Glu-Ala-Leu-Asn-Arg-Trp-Ile-Thr (SEQ ID NO:17)
((pep25) Glu-Val-Leu-Asn-Arg-Trp-Ile-Thr (SEQ ID NO:18)
(pep26) Glu-Phe-Ala-Asn-Arg-Trp-Ile-Thr (SEQ ID NO:19)
(pep27) Glu-Phe-Leu-Ala-Arg-Trp-Ile-Thr (SEQ ID NO:20)
(pep28) Glu-Phe-Leu-Asn-Ala-Trp-Ile-Thr (SEQ ID NO:21)
(pep29) Glu-Phe-Leu-Asn-Glu-Trp-Ile-Thr (SEQ ID NO:22)
(pep30) Glu-Phe-Leu-Asn-Arg-Ala-Ile-Thr (SEQ ID NO:23)
(pep31) Glu-Phe-Leu-Asn-Arg-Trp-Ala-Thr (SEQ ID NO:24)
(pep32) Glu-Phe-Leu-Asn-Arg-Trp-Ile-Ala (SEQ ID NO:25)
(pep33) Glu-Phe-Leu-Asn-Arg-Trp-Ile-Thr-NH$_2$ (SEQ ID NO:26) and, (pep34, linear) and (pep35, cyclic) Cys-Glu-Phe-Leu-Asn-Arg-Trp-Ile-Thr-Ala-Cys (SEQ ID NO:27).

In a further preferred embodiment, the present invention relates to the synthetic anti-inflammatory peptide Arg-Met-Leu-Thr (pep3), and to anti-inflammatory peptides resulting from the modification thereof by:

(a) elongation by up to 4 further amino acid residues at the C and/or N terminal end, such as in pep45, or preferably according to the natural sequence of IL-2;

(b) substitution of the Arg residue by a natural or non-natural positively charged amino acid residue, preferably selected from Lys, Orn, homoArg, diaminobutyric acid, (c) substitution of the Met residue by a natural or non-natural hydrophobic, aliphatic or aromatic, amino acid residue, preferably selected from Phe, Tyr, Ile, Leu, Nle, Tic;

(d) substitution of the Leu residue by a natural or non-natural hydrophobic, aliphatic or aromatic, amino acid residue, preferably selected from Phe, Tyr, Nle, Tic;

(e) substitution of the Thr residue by an aliphatic hydrophobic amino acid residue such as Ala, Ile, Leu, or a hydroxy- or thio-containing amino acid residue such as Ser, Cys;

(f) amidation of the C-terminal Thr residue;

(g) cyclization of pep3 or of any peptide of (a) to (f); and (h) any combination of (a) to (g).

Examples of such modified peptides derived from pep3 include;

(pep36) Ala-Met-Leu-Thr (SEQ ID NO:28)
(pep37) Arg-Ala-Leu-Thr (SEQ ID NO:29)
(pep38) Arg-Met-Ala-Thr (SEQ ID NO:30)
(pep39) Arg-Met-Leu-Ala (SEQ ID NO:31)
(pep40) Lys-Met-Leu-Thr (SEQ ID NO:32)
(pep41) Arg-Val-Leu-Thr (SEQ ID NO:33)
(pep42) Arg-Met-Leu-Thr-NH$_2$ (SEQ ID NO:34)
(pep43) Pro-Lys-Leu-Thr-Arg-Met-Leu-Thr (SEQ ID NO:35)
(pep44) Arg-Met-Leu-Thr-Phe-Lys-Phe-Tyr (SEQ ID NO:36) and,
(pep45, linear) and (pep46, cyclic) Cys-Arg-Met-Leu-Thr-Ala-Cys (SEQ ID NO:37).

The peptides and peptide derivatives of the invention are obtained by any method of peptide synthesis known to those skilled in the art, such as for example by solid phase peptide synthesis.

The present invention is also directed to pharmaceutical compositions comprising a pharmaceutically acceptable carrier and at least one anti-inflammatory peptide or peptide derivative of the invention. The pharmaceutical composition will be administered according to known modes of peptide administration, including oral, intravenous, subcutaneous, intraarticular, intramuscular, inhalation, intranasal, intrathecal, intradermal, transdermal or other known routes. The dosage administered will be dependent upon the age, sex, health condition and weight of the recipient, and the nature of the effect desired.

The peptides of the invention for use in therapy are typically formulated for administration to patients with a pharmaceutically acceptable carrier or diluent to produce a pharmaceutical composition. The formulation will depend upon the nature of the peptide and the route of administration but typically they can be formulated for topical, parenteral, intramuscular, intravenous, intraperitoneal, intranasal inhalation, lung-inhalation, intradermal or intra-articular administration. The peptide may be used in an injectable form. It may therefore be mixed with any vehicle which is pharmaceutically acceptable for an injectable formulation, preferably for a direct injection at the site to be treated, although it may be administered systemically.

The pharmaceutically acceptable carrier or diluent may be, for example, sterile isotonic saline solutions, or other isotonic solutions such as phosphate-buffered saline. The peptides of the present invention may be admixed with any suitable binder(s), lubricant(s), suspending agent(s), coating agent(s), solubilising agent(s). It is also preferred to formulate the peptide in an orally active form.

Tablets or capsules of the peptides may be administered singly or two or more at a time, as appropriate. It is also possible to administer the peptides in sustained release formulations.

Typically, the physician will determine the actual dosage which will be most suitable for an individual patient and it will vary with the age, weight and response of the particular patient. There can, of course, be individual instances where higher or lower dosage ranges are merited, and such are within the scope of this invention.

Alternatively, the peptides of the invention, can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavouring and colouring agents. For such oral administration, the peptide may preferably formed into microcapsules or nanoparticles together with biocompatible polymers such as poly-lactic acid and the like.

The compositions (as well as the peptides alone) can also be injected parenterally, for example intracavernosally, intravenously, intramuscularly or subcutaneously. In this case, the compositions will comprise a suitable carrier or diluent. For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

The peptides and peptide derivatives of the invention are for use in the treatment of or amelioration of acute and chronic inflammatory disorders including, but not being limited to, autoimmune diseases such as rheumatoid arthritis, diabetes type I, multiple sclerosis, systemic lupus erythematosus, uveitis, bowel inflammation and Crohn's disease.

The present invention further relates to a method of treatment of a patient suffering from an inflammatory disorder which comprises administering to said patient an effective amount of a peptide or peptide derivative of the invention.

The invention will now be illustrated by the following non-limiting Examples.

EXAMPLES

Material and Methods

Materials. The following reagents were obtained as indicated. Recombinant human IL-2 (sp. act. 18×10⁶ U/mg; Chiron B. V., Amsterdam, The Netherlands); recombinant human IL-7 (sp. act. 2×10⁵ U/mg; Immunex Corp., Seattle, Wash.); recombinant human macrophage inflammatory protein MIP-1β (Pepro Tech, Rocky Hill, N.J.); recombinant human TNF-α (Boehringer, Ingelheim, Germany); Affi-gel 10 beads (Pharmacia, N.J.); fibronectin (FN) (Chemicon; Temecula, Calif.); BSA, laminin (LN), PMA, and TRITC-conjugated phalloidin (Sigma Chemical Co., St. Louis, Mo.); collagen type IV (CO-IV, ICN, Costa Mesa, Calif.); and HEPES buffer, antibiotics, heat-inactivated FCS, sodium pyruvate, DMEM, CSS and RPMI-1640 (Beit-Haemek, Israel). An anti-$β_1$ integrin-specific affinity-modulating mAb, 8A2, was donated by Dr. J. M. Harlan (Washington University, Seattle, Wash.). All protected amino acids, coupling reagents, and polymers were obtained from Nova Biochemicals (Läufelfingen, Switzerland). Synthesis-grade solvents were obtained from Labscan (Dublin, Ireland). HPLC solvents and columns were obtained from Merck (Darmstadt, Germany).

Human colonic epithelial cell lines HT-29 (ATCC HTB38) and Caco-2 (ATCC HTB27) were obtained from the American Type Culture Collection (ATTC, Rockville, Md.). Cells were maintained in culture medium (DMEM supplemented with 10% cosmic calf serum (CSS), 2 mM glutamine, 100 U/ml penicillin, and 0.1 mg/ml streptomycin), at 37° C. and atmosphere of 5%, $CO_2$. Cell viability was assessed using the standard MTT method.

T cell adhesion assays. Human T cells were purified from the peripheral blood of healthy donors, and T cell adhesion to immobilized protein substrates was examined as follows: Human leukocytes were isolated on a Ficoll gradient, washed, and incubated (2 h, 37° C., 7.5% $CO_2$, humidified atmosphere) on petri dishes. The non-adherent cells were then collected and incubated (1 h, 37° C., 7.5% $CO_2$, humidified atmosphere) on nylon wool columns (Novamed Ltd., Jerusalem, Israel). Unbound cells were eluted from the columns by extensive washings. The resulting cell population was always >92% T cells. Intact IL-2 or IL-2-derived peptides (in 50 μl) were added to flat-bottom microtiter wells that had been pre-coated with ECM or ECM proteins (FN or LN; 1 μg/well) and blocked with 0.1% BSA. After 4–6 h at 37° C., the wells were washed and $^{51}$[Cr]-labeled T cells were added to the wells, 10⁵ cells/100 μl of adhesion medium (RPMI-1640 supplemented with 0.1% BSA, 1% sodium pyruvate, 1% HEPES buffer). The microtiter plates containing the cells were incubated (30 min, 37° C.) in a humidified, 7.5% $CO_2$ atmosphere, and then washed. The adherent cells were lysed, and the resulting supernatants were removed and analyzed in a γ-counter. For each experimental group, the results were expressed as the mean percentage ±SD of bound T cells from quadruplicate wells. To some wells, different concentrations of soluble IL-2 were added concomitantly with the T cells, and with others, different concentrations of elastase-degraded IL-2-derived fractions, or the corresponding synthetic peptides, were added together with stimulators [PMA (50 ng/ml), IL-7 (50 ng/ml), MIP-1β (20 ng/ml), 8A2 (1 μg/ml), mAb anti-CD3 (1 μg/ml), or IL-2 (10 U/ml)].

Chemotaxis assays. T cell chemotaxis was performed and analyzed as previously described (Ben-Baruch et al., 1997). Briefly, the migration of human T cells (0.5×10⁶ cells in adhesion medium/well) was examined in a 48-well chemotaxis micro-chamber (Neuro-Probe Inc., Cabin John, M D).

The two compartments of the micro-chambers were separated by a FN-coated polycarbonate filter (5 μm pore size; Osmonics Protein Products, Livemore, Calif.). Where indicated, MIP-1μ or IL-2 was added to the lower wells, and the T cells were added to the upper chambers together with the peptides. After incubation (120 min, 37° C., in a humidified, 7.5% $CO_2$ atmosphere); the filters were removed, fixed, and stained with a Diff-Quik staining kit Dade, Düdingen, Switzerland). The number of migrating T cells in five high-power fields (under 500× magnification; WILD Microscope, Heerbrugg, Switzerland) was evaluated. For each group, the results are expressed as the mean number of cells in one high-power field.

Spontaneous or cytokine-induced secretion of IL-8 or IL-1β from intestinal epithelial cell. Test cells (HT-29 or Caco-2) were grown as confluent monolayers in 24-well tissue culture plates. After the cells reached confluence, the culture medium was changed and the cells (10⁶ cells/well) were incubated for 24 h at 37° C. with the IL-2 peptides (or control and derivative peptides) in 24-well plates without (spontaneous) or with the addition of TNF-α (TNF-α-induced). When TNF-α was used, the peptides were added to the cells 1 hour prior to the addition of TNF-α. Following culture, the supernatants were harvested and analyzed for IL-8 or IL-1β secretion by ELISA using commercially available kits for IL-8 (Pharmingen) and IL-1β (Genzyme), according to the manufacturers' protocols.

Purification of elastase and elastase digestion of IL-2. Neutrophils were isolated from the whole blood of a healthy donor by dextran sedimentation and Ficoll-Hypaque gradient centrifugation, as previously described (Yavin et al., 1996). Elastase was isolated by aprotinin-Sepharose affinity chromatography, followed by carboxymethyl-cellulose ion exchange chromatography, as developed by Baugh and Travis (Yavin et al., 1996; Baugh and Travis, 1976). The purified elastase, which was lyophilized and stored at −20° C. until used, was biochemically checked to be entirely free from cross-contamination with cathepsin G (not shown). IL-2 was dissolved in distilled water to yield a 1 mg/ml solution. Lyophilized neutrophil elastase (50 μg) was dissolved in 1 ml of PBS and immediately added to the IL-2 solution. The elastase-IL-2 mixture was incubated (12 h) at 37° C. Aliquots were removed and stored at −20° C. until subjected to HPLC separation.

Reverse phase HPLC. Elastase digests of IL-2 were purified with a prepacked Lichrospher-100 RP-18 column (4×25 nm, 5 μm bead size), using a binary gradient formed with 0.1% trifluoroacetic acid (TFA) in $H_2O$ (solution A) and 0.1% TFA in 75% acetonitrile in $H_2O$ [(solution B) at t=0 min, B=3.5%, at t=5 min, B=3.5%, and then, the concentrations began to increase: at t=60 min, B=100% (i.e. 75% acetonitrile)]. The flow-rate was constant on 0.8 ml/min. A Spectra-Physics SP8800 liquid chromatography system (Fremont, Calif.) equipped with an Applied Biosystems 757 (Foster City, Calif.) variable wavelength absorbency detector was used. The column effluents were monitored by UV absorbency at 220 nm, and the chromatograms were recorded on a ChromeJet integrator. Fractions that were 20% or more above valley levels were pooled, rotoevaporated to a minimal volume, and diluted with HPLC grade water. The rotoevaporation and dilution with water step was performed twice to remove residual TFA and acetonitrile.

Amino acid composition of the synthetic peptides and amino acid sequence analysis. Purified peptide solutions [≈40 μg of peptide in 40 μl, with 5 μg of norvaline (an unnatural amino acid) as an internal standard] were rotoevaporated, hydrolyzed (10° C., 22 h) in 6N HCl under vacuum, and analyzed with an amino acid analyzer (HP1090, Palo Alto, Calif.). An on-line pre-column ortho-phthalaldehyde (OPA)/9-fluorenylmethoxycarbonyl (F-moc) derivatization, combined with reverse phase chromatography, was used to determine the amino acid composition of the peptides and the total peptide yield. Without exception, all of the peptides yielded excellent analysis ratios of corresponding amino acids deviations from expected values of less than 10%. Analysis of the elastase-generated IL-2 fractions was performed using a Model 470A gas phase microsequencer. Phenylthiohydantoin amino acid derivatives were separated on-line by reverse phase HPLC on a PTH C-18 column (2.1×220 mm) using a Model 120A analyzer (Applied Biosystems, CA).

Solid phase peptide synthesis. IL-2-derived peptides were prepared by conventional solid phase peptide synthesis, using an AMS-422 automated solid phase multiple peptide synthesizer (Abimed, Langenfeld, Germany). The Fmoc strategy was used for peptide chain assembly, according to the commercial protocol. In each reaction vessel, we used 12.5 $\mu$mol of Wang resin containing the first covalently bound corresponding N-Fmoc C-terminal amino acid (typically, polymer loadings of 0.3–0.7 mmol/g resin were used). Fmoc deprotection was achieved by two consecutive treatments with 20% piperidine in dimethyl formamide, usually 10–15 each min at 22° C., depending on the length of peptide and the Fmoc-protected amino acid type. The protecting groups used for the side chain of the amino acids were tert-butyloxycarbonyl for Trp and Lys; trityl for Asn, Cys, Gln and His; tert-butylester for Asp and Glu; and tert-butylether for Ser, Tyr and Thr. Usually, coupling was achieved using two successive reactions (typically 20–45 min each at 22° C., depending on the length of peptide and amino acid derivative type) with 50 $\mu$mol (4 eqv) of N-Fmoc-protected amino acid, 50 $\mu$mol (4 eqv) of benzotriazole-1-yl-oxy-tris-pyrolidino-phosphonium hexafluorophosphate (PyBop) reagent, and 100 $\mu$mol (8 eqv) of N-methylmorpholine were all dissolved in dimethylformamide (DMF). The peptide was cleaved from the polymer by reacting (2 h, 22° C.) the resin with trifluoroacetic acid/$H_2O$/triethylsilane (90/5/5; v/v/v). The solution containing the crude, unprotected peptides was then cooled down to 4° C., precipitated with ether (4° C.), and centrifuged (15 min, 3000 rpm, 4° C.). The pellet was washed and centrifuged (×3) with ether, dissolved in 30% acetonitrile in $H_2O$, and lyophilized. The lyophilized material was reconstituted in double distilled water before use, only the stock solution, not the diluted material, was stored at −20° C.

Synthesis of cyclic peptides. The linear peptides pep12, pep14, pep35, pep46 were cyclicized as follows: 0.5–1.0 mg of SH-free peptide was dissolved in 1 ml of ammonium acetate buffer (0.1N, pH 7.0). A solution of $K_3[Fe(CN)_6]$ (1–5 mM) in the same buffer was slowly added to the stirred peptide solution at room temperature, in a titrimetric fashion until a stable faint yellowish color was apparent. The solution revealed a negative 5,5'-dithio-bis(2-nitrobenzoic acid (DTNB; Ellman's Reagent)-test for free SH. Lyophilization and purification by HPLC were then performed as usual.

Staining of actin cytoskeleton. T cells were incubated (18 h, 37° C., 7.5% $CO_2$, humidified atmosphere) in culture medium. IL-2 or PMA was added to the cell cultures, which were then incubated for 24 h. The T cells were then washed and seeded onto FN-covered coverslips in the presence of either PMA (50 ng/ml), IL-2 (100 U/ml), or IL-2 peptides (0.1 ng/ml). After 1 h at 37° C., the adherent cells were fixed (3 min) with paraformaldehyde (3%) and Triton X-100 (0.5%), washed, and fixed (20 min) again with paraformaldehyde (3%). The fixed adherent cells were washed, treated with TRITC-phalloidin, and washed again. Photographs (×1000 magnification) were then taken.

Example 1

Figure 1B:
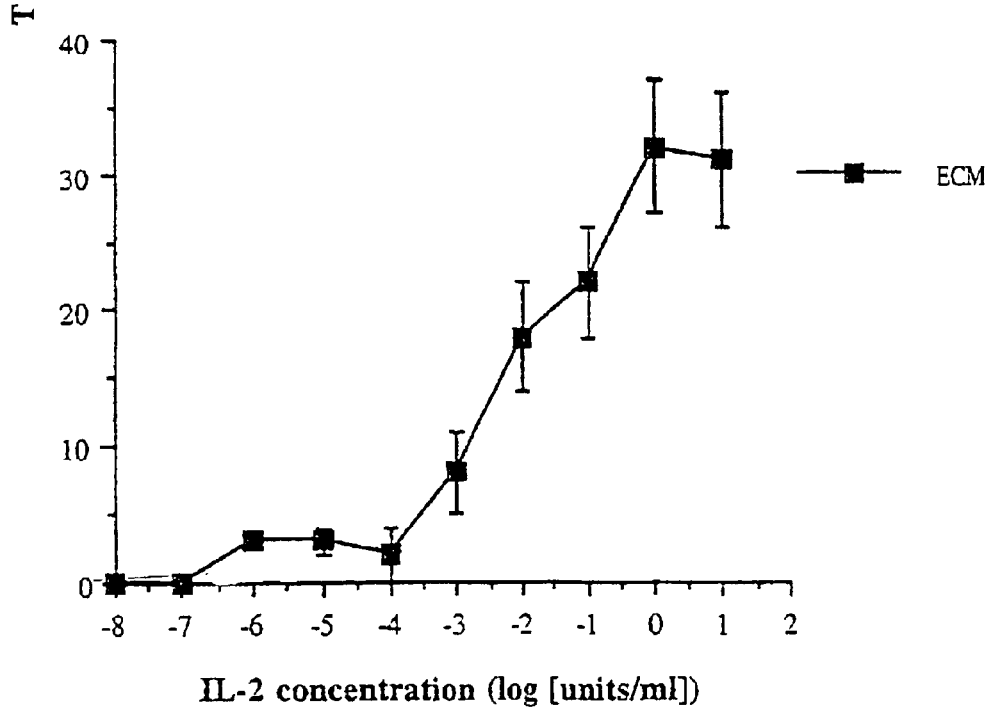

Induction of the adhesion of T cells to ECM, FN, LN, and CO-IV by IL-2. We examined the ability of soluble IL-2 to induce adhesion of human T cells to ECM, FN, LN, and CO-IV. The results indicated that IL-2 induced T cell adhesion to FN, LN, and CO-IV (FIG. 1A), as well as to intact ECM (FIG. 1B). Note that the adhesion of T cells to LN induced by IL-2 was lower than that induced to the other ECM glycoproteins. When T cells were activated only with PMA, 45±4.4% of them adhered to immobilized ECM and ECM glycoproteins (not shown). IL-2-induced T cell adhesion to the ECM glycoproteins was inhibited by anti-human $\beta_1$ integrin mAbs (not shown), which suggests that the pro-adhesive effects of IL-2 were induced via cell surface-expressed integrins. However, under our experimental conditions, IL-2 did not alter the T cell surface expression of $\beta_1$ integrins (not shown). Thus IL-2, in addition to other pro-inflammatory mediators, appears to regulate the adhesiveness of resting human T cells to immobilized ECM and ECM glycoproteins.

Example 2

Figure 2:
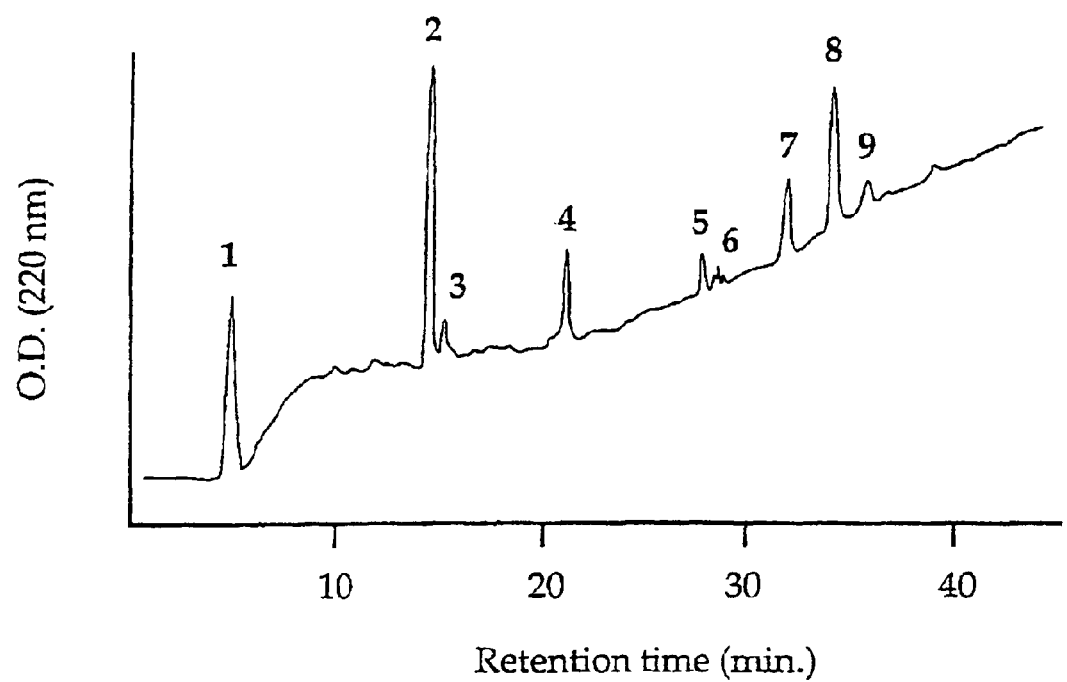
FIG. 2 depicts a chromatogram of IL-2 fractions obtained upon elastase proteolysis. IL-2 (1 mg/ml) was incubated (12 hr, 37° C.) with neutrophil elastase (50 $\mu$g/ml in PBS). The resulting enzymatic digests were purified by HPLC. Fraction 1 consisted of salts used for the separation procedure. One experiment representative of three.

The effects of IL-2 fragments obtained by elastase degradation on the interaction of T cells with FN. We have assumed that the degradation of IL-2 can occur in the inflamed milieu in which both cytokines, such as IL-2, and proteolytic enzymes, such as neutrophil elastase, are present. We also hypothesized that, in contrast to the intact IL-2 molecule, certain portions of IL-2 can abrogate the adhesiveness of activated T cells to ECM ligands. Hence, elastase and soluble IL-2 were incubated together at physiologic conditions. HPLC analysis of the elastase-degraded IL-2 revealed at least 8 peaks of IL-2, each of which represented at least one low molecular weight protein fragment (FIG. 2).

Figure 3:
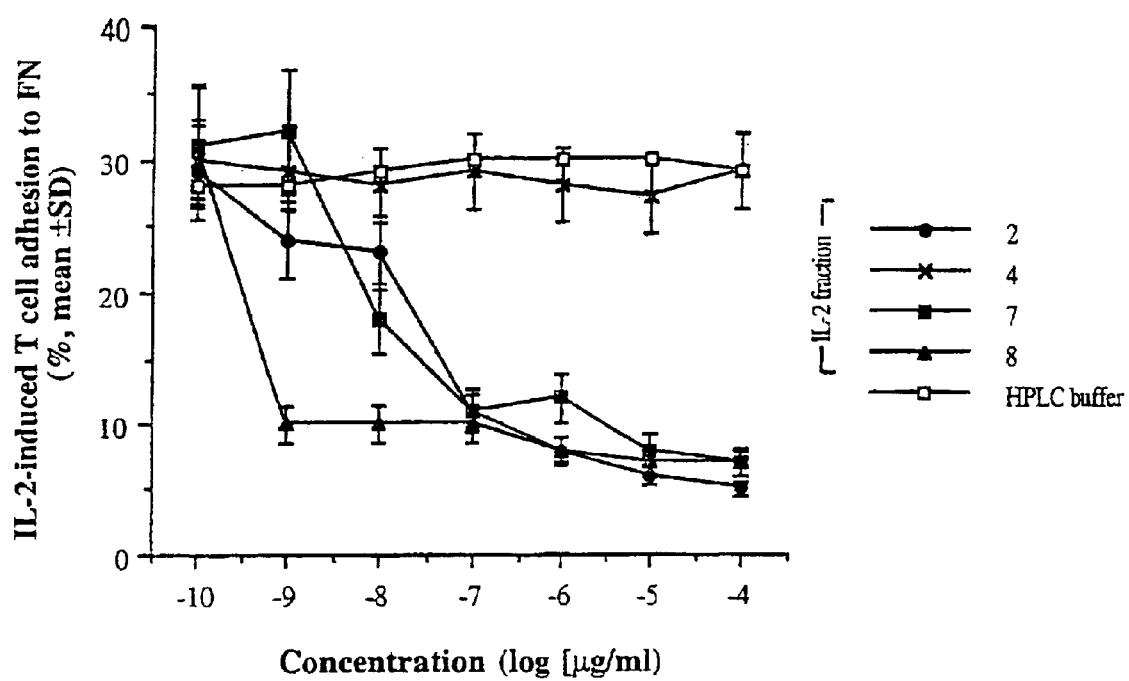
FIG. 3 shows effects of IL-2 fractions, generated by elastase degradation, on the IL-2-induced adhesion of T cells to FN. IL-2 (10 U/ml)-stimulated [$^{51}$Cr]-labeled T cells were seeded, in the presence or absence of elastase-generated IL-2 protein products, onto wells coated with FN. After 30 min at 37° C., non-adherent T cells were removed, and the percentage of adhered cells was determined. One experiment representative of six.

Next, we examined the ability of the HPLC-purified IL-2 fractions, which were generated by elastase-degradation, to inhibit soluble IL-2-induced interactions of T cells with FN. We chose to investigate the major peaks of HPLC-purified, elastase-degraded fractions of IL-2. Fractions 2, 7, and 8 inhibited the adhesion of T cells to immobilized FN in a dose-dependent and statistically significant fashion, whereas fractions 4 and the HPLC buffer did not (FIG. 3). Thus, certain IL-2 fragments, obtained by neutrophil elastase-processing of the cytokine, can inhibit IL-2-induced adhesion of T cells to FN.

Example 3

Figure 4A:
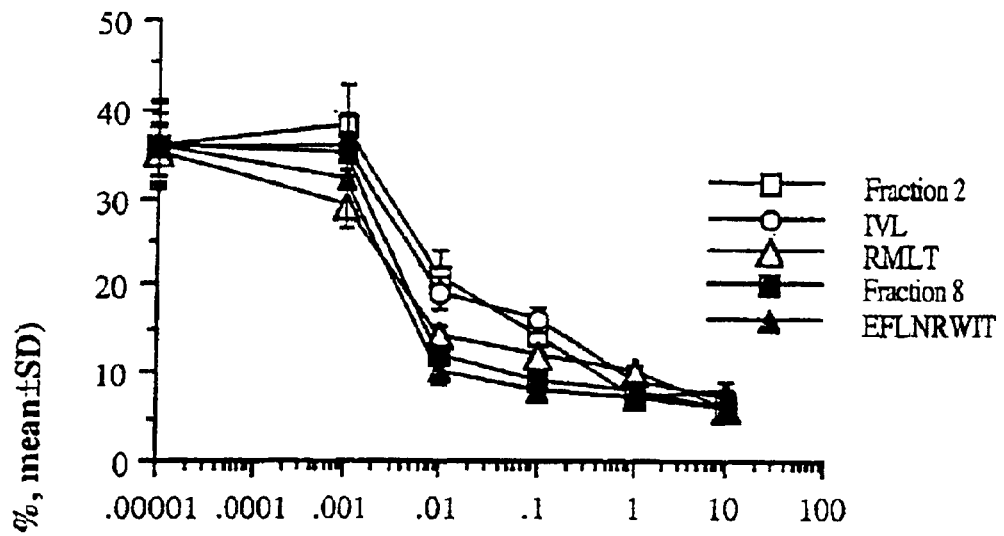
FIGS. 4A–4C show specific inhibition, by elastase-generated fractions 2 and 8 of IL-2 and by their synthetic peptides, of IL-2-induced T cell adhesion to FN.

The effect of synthetic peptides, with putative amino acid compositions corresponding to fractions 2 and 8, on IL-2-induced T cell adhesion to FN. Next, the primary sequence of fractions 2 and 8 were analyzed by gas phase chromatography, because these elastase-generated fractions of IL-2 appeared to contain adhesion-suppressive peptides. Our analysis revealed that fragment 2 contained an Ile-Val-Leu (IVL; pep1; IL-$2_{112-114}$) and an Arg-Met-Leu-Thr (RMLT; pep2; IL-$2_{58-61}$) peptide (SEQ ID NO:2), whereas fragment 8 contained a Glu-Phe-Leu-Asn-Arg-Trp-Ile-Thr (EFLNRWIT; pep3; IL-$2_{136-143}$) octa-peptide (SEQ ID NO:1). These three peptides were synthesized, and their effects on IL-2-induced T cell adhesion to FN were studied. The Ile-Val-Leu, Arg-Met-Leu-Thr (SEQ ID NO:2), and Glu-Phe-Leu-Asn-Arg-Trp-Ile-Thr (SEQ ID NO:1), inhibited, in a dose-dependent manner, the adhesion of IL-2-activated T cells to FN; the Arg-Met-Leu-Thr (SEQ ID NO:2) is apparently the most potent inhibitor (FIG. 4A). Maximum inhibition was achieved with about 0.1 pg/ml (0.2 pM) for Arg-Met-Leu-Thr (SEQ ID NO:2), and 1 pg/ml of either Ile-Val-Leu or Glu-Phe-Leu-Asn-Arg-Trp-Ile-Thr (SEQ ID NO:1) (2.91 and 0.92 pM, respectively). The inhibitory dose-response curves of Ile-Val-Leu and Glu-Phe-Leu-Asn-Arg-Trp-Ile-Thr (SEQ ID NO:1) are similar to those of the HPLC fractions 2 and 8, respectively, from which they were derived.

Figure 4B:
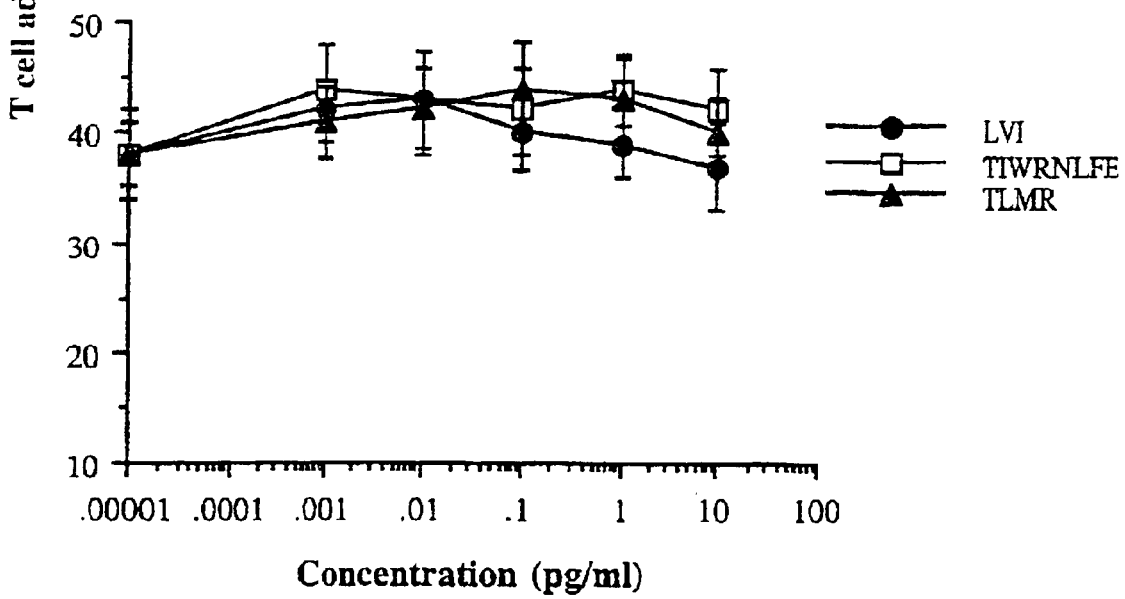

To examine the specificity, on the biologic and chemical levels, of the inhibition of T cell adhesion by the elastase-generated, synthetic IL-2 peptides, we synthesized the three IL-2 peptides in their inverse amino acid sequences, Leu-Val-Ile, Thr-Leu-Met-Arg (SEQ ID NO:38), and Thr-Ile-Trp-Arg-Asn-Leu-Phe-Glu (SEQ ID NO:39), and then tested their effects on IL-2-induced T cell adhesion to FN. The results, shown in FIG. 4B, indicate that none of these peptides, tested in a broad range of dosages, interfere with T cell adhesion. Thus, the anti-adhesive effects of Ile-Val-Leu and Glu-Phe-Leu-Asn-Arg-Trp-Ile-Thr (SEQ ID NO:1) peptides of IL-2 appear to be due to their direct biologic effect on responding lymphocytes.

Figure 4C:
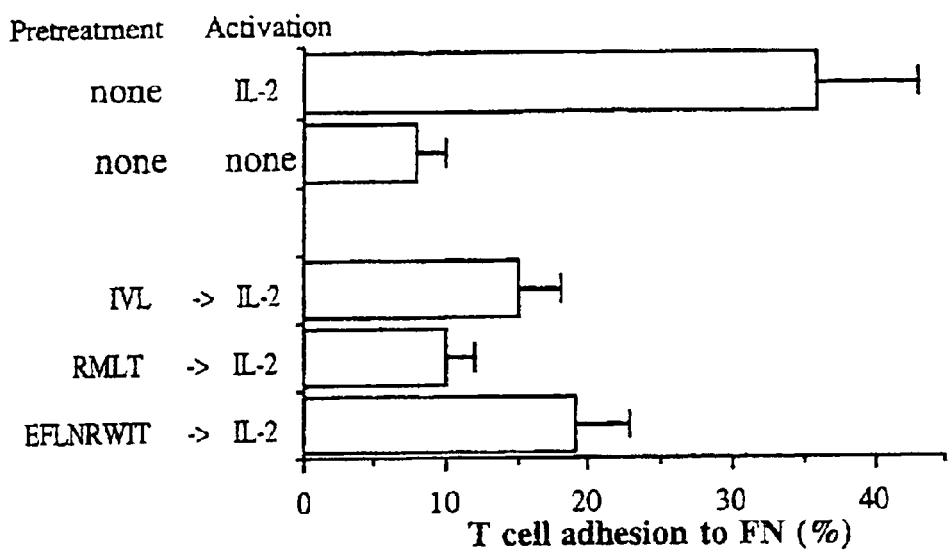

Do the IL-2 peptides, Ile-Val-Leu, Arg-Met-Leu-Thr (SEQ ID NO:2), and Glu-Phe-Leu-Asn-Arg-Trp-Ile-Thr (SEQ ID NO:1) have to be present during the entire period of the assay to exert their inhibitory effects? The results, shown in FIG. 4C, indicate that most of the anti-adhesive effects of the three peptides persevered even if these peptides (at 1 pg/ml) were removed from the T cells prior to their activation with IL-2 and seeding onto the FN-coated surfaces. Apparently, their prolonged inhibitory potential may involve active intracellular signaling pathways. These results suggest that the IL-2 peptides neither exert their inhibitory activities on T cell adhesion to FN via binding to the ECM protein, nor to FN-specific $\beta_1$ integrins expressed on the adhering T cells.

Example 4

Figure 5:
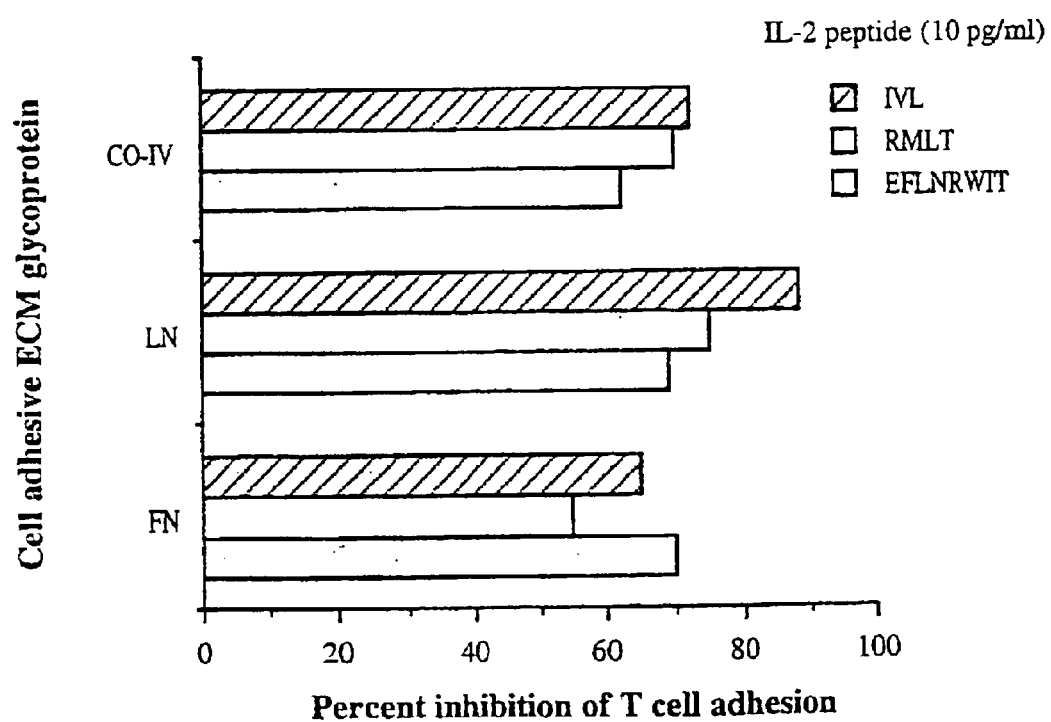
FIG. 5 shows inhibition by the IL-2 peptides pep1, pep2 and pep3, of T cell adhesion to LN; CO-IV and FN. T cells were pre-treated with the indicated IL-2 peptides (10 pg/ml, 30 min, 37° C., 10% $CO_2$, humidified atmosphere) and then with IL-2 (10 U/ml). The T cells were then seeded onto microtiter wells that were pre-coated (1 μg/well) with the various ECM glycoproteins. T cell adhesion was measured 30 min later.

Ile-Val-Leu, Arg-Met-Leu-Thr (SEQ ID NO:2) and Glu-Phe-Leu-Asn-Arg-Trp-Ile-Thr (SEQ ID NO:1) inhibit T cell adhesion to LN, CO-IV and FN. The next experiment was designed and performed to verify that the three IL-2-derived peptides indeed affect T cell interactions with ECM glycoproteins other than FN. T cells were pre-exposed to the three peptides (at 10 pg/ml), and then activated with IL-2. The treated cells were then added to microtiter wells coated with CO-IV, LN, and FN. The results, shown in FIG. 5, indicate that both Ile-Val-Leu, Arg-Met-Leu-Thr (SEQ ID NO:2), and Glu-Phe-Leu-Asn-Arg-Trp-Ile-Thr (SEQ ID NO:1) inhibit T cell adhesion to the three major cell-adhesive glycoproteins of the ECM (FIG. 5), suggesting that the elastase-generated IL-2 peptides exert their inhibitory effects over different subsets of $\beta_1$ integrins.

Example 5

Figure 6:
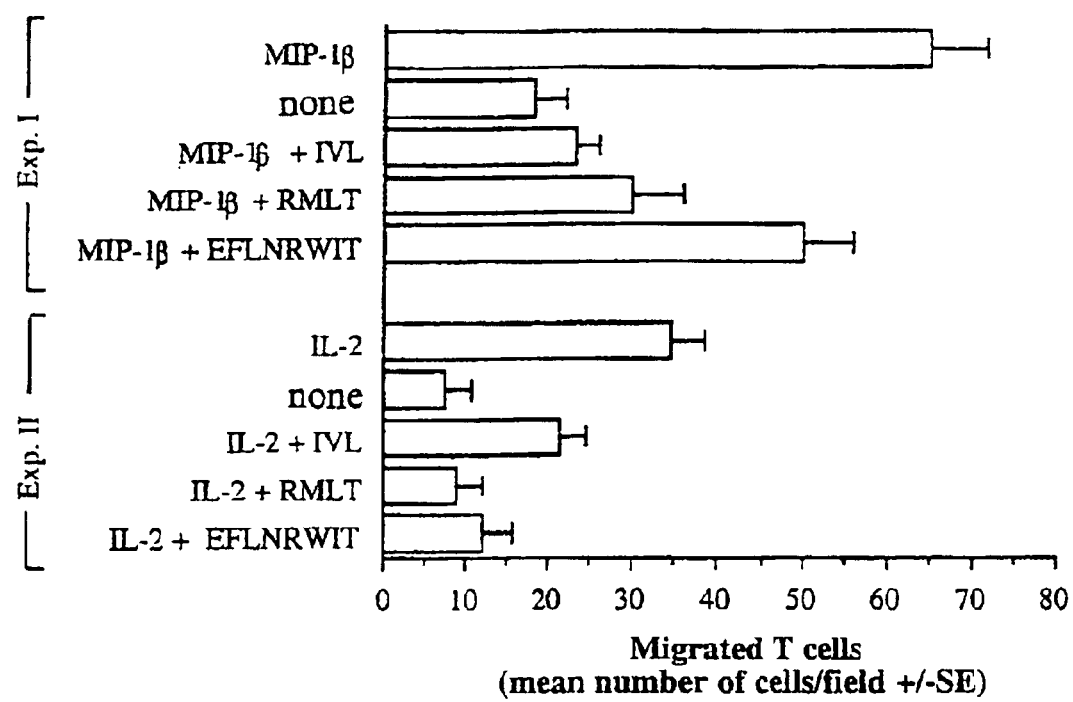
FIG. 6 shows inhibition of IL-2-induced T cell migration through FN by pep1 and pep3. T cells were pre-treated with the IL-2 peptides (1 pg/ml) or buffer alone and then placed in the upper wells of a chemotaxis chamber, in which IL-2 (10 U/ml) or MIP-1β (10 ng/ml) had been added to the lower compartment. T cell migration towards the chemotactic sources was assessed after 2 hr. One experiment representative of four.

Ile-Val-Leu and Glu-Phe-Leu-Asn-Arg-Trp-Ile-Thr (SEQ ID NO:1) inhibit T cell chemotactic migration induced by IL-2 or MIP-1β. Immune cell migration is the outcome of a subtle biological equilibrium existing between adhesion and detachment events. Lymphocyte adhesion to the subendothelial ECM and subsequent migration are two active processes that can overlap, but are not mutually dependent events. Adhesion and migration may depend on the ability of the T cells to continuously integrate different pro- and anti-adhesive signals via their versatile receptors for ECM, chemokines, cytokines, and possibly, also antigenic moieties. Therefore, we next examined the effects of the Ile-Val-Leu, Arg-Met-Leu-Thr (SEQ ID NO:2), and Glu-Phe-Leu-Asn-Arg-Trp-Ile-Thr (SEQ ID NO:1) peptides (at 1 pg/ml) on the IL-2- and MIP-1β-induced T cell chemotaxis through FN-coated polycarbonate membranes. The gradient generated by MIP-1β and IL-2, which were placed in the lower compartment of the 48-well chemotaxis apparatus, induced a marked T cell migration through FN-coated membranes, which was about 3 to 4-fold higher than the control (FIG. 6). Both Ile-Val-Leu, Arg-Met-Leu-Thr (SEQ ID NO:2), and Glu-Phe-Leu-Asn-Arg-Trp-Ile-Thr (SEQ ID NO:1) markedly ($p<0.01$) inhibited T cell migration toward IL-2, by about 30, 90, and 60%, respectively. However, although the Ile-Val-Leu peptide, and to a lesser degree also the Arg-Met-Leu-Thr (SEQ ID NO:2) peptide, markedly inhibited (80% and 60%, respectively) T cell chemotaxis toward MIP-1β, the Glu-Phe-Leu-Asn-Arg-Trp-Ile-Thr (SEQ ID NO:1) showed only a limited inhibitory effect on the chemokine-induced T cell chemotaxis. Thus, in addition to the capacity of the Ile-Val-Leu and Glu-Phe-Leu-Asn-Arg-Trp-Ile-Thr (SEQ ID NO:1) peptides to inhibit T cell-ECM adhesion, they seem to inhibit T cell migration through FN in response to a diffusible gradient produced by IL-2 or MIP-1β.

Example 6

Figure 7A:
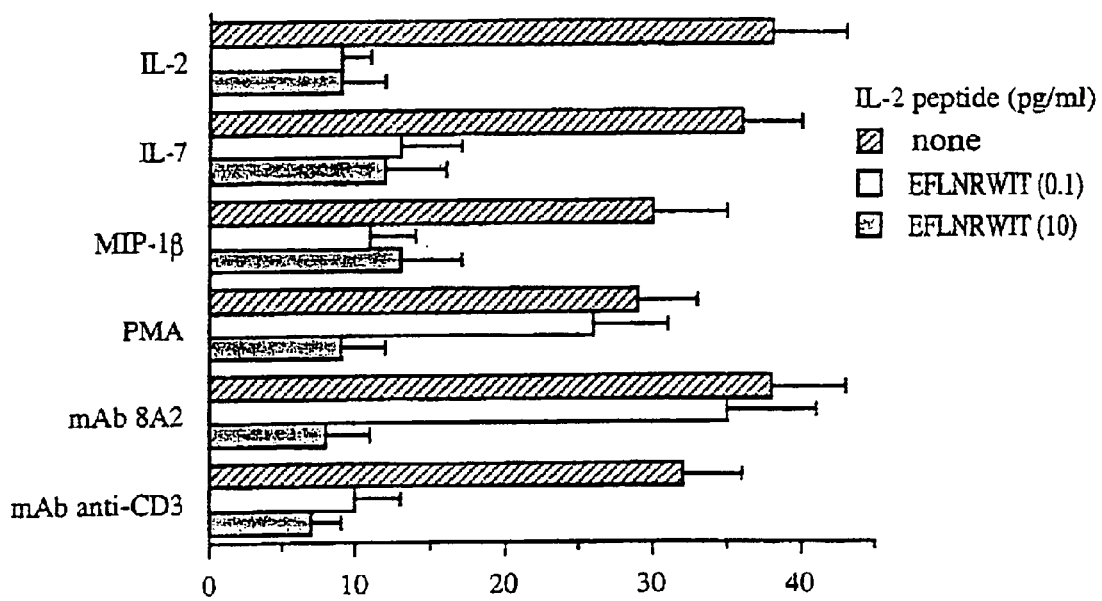
FIGS. 7A–7B show inhibition by pep2 (FIG. 7A) and pep1 (FIG. 7B) of T cell adhesion to FN, induced by various activators. Labeled T cells were seeded onto FN-coated wells in the presence of IL-2 (10 U/ml), IL-7 (50 ng/ml), MIP-1β (20 ng/ml), PMA (50 ng/ml), 8A2 mAb. (1 μg/ml), or anti-human CD3 mAb (1 μg/ml). The IL-2-derived peptides, pep1 or pep2, were also present in some wells. After 30 min at 37° C., non-adherent T cells were removed by washing, the remaining adherent cells were lysed, and the percentage of T cells that had adhered was determined. One experiment representative of four.
Figure 7B:
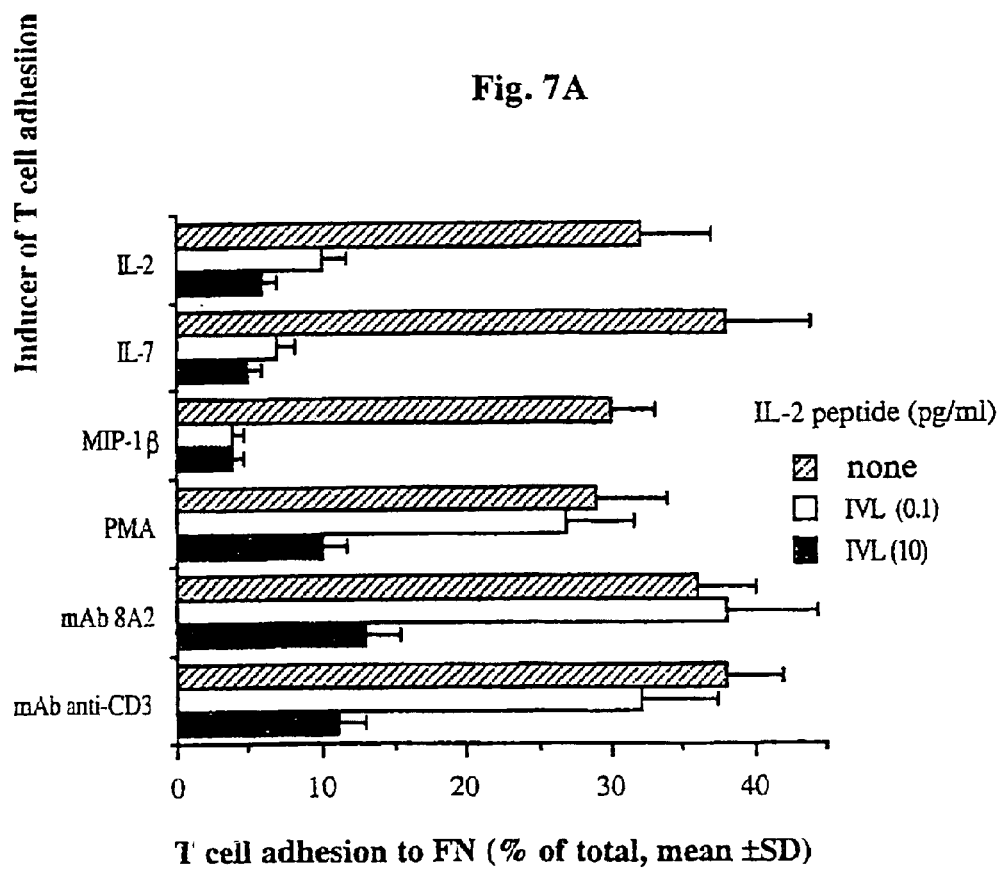

Inhibition by the Ile-Val-Leu and Glu-Phe-Leu-Asn-Arg-Trp-Ile-Thr (SEQ ID NO:1) peptides of T cell adhesion to FN induced by various pro-inflammatory mediators and by mAb specific for molecules expressed on T cells. The preceding chemotaxis experiments indicated that the Ile-Val-Leu and Glu-Phe-Leu-Asn-Arg-Trp-Ile-Thr (SEQ ID NO:1) peptides can inhibit T cell adhesion and migration through FN barriers induced not only by IL-2, but also by the chemokine MIP-1β. Therefore, in an attempt to further understand the possible physiologic relevance of such phenomena, we examined the ability of these peptides to inhibit the adhesion to FN of T cells stimulated by modes other than IL-2. At 10 pg/ml, both Glu-Phe-Leu-Asn-Arg-Trp-Ile-Thr (SEQ ID NO:1) and Ile-Val-Leu inhibited T cell adhesion to FN that was induced by various stimulators of T cells and modulators of the $\beta_1$ integrin functions tested (FIG. 7). However, at 0.1 pg/ml, Glu-Phe-Leu-Asn-Arg-Trp-Ile-Thr (SEQ ID NO:1) did not inhibit the PMA- and 8A2-induced adhesion, and the Ile-Val-Leu peptide did not inhibit PMA-, 8A2-, and anti-CD3 mAb-induced T cell adhesion to FN, which indicates that these modes of activation are less susceptible to IL-2-derived peptide-induced suppression than IL-2-mediated activation. In experiments similar to those shown in FIGS. 7A and 7B, the control peptides (corresponding inverse sequences) did not affect T cell adhesion to FN induced by the indicated activators (data not shown). Hence, Glu-Phe-Leu-Asn-Arg-Trp-Ile-Thr (SEQ ID NO:1) and Ile-Val-Leu apparently inhibit T cell adhesion to the FN component of ECM via a common intracellular event that is linked to the regulation of the avidities and affinities of $\beta_1$ integrins, and therefore, to their ligand recognition and binding.

Example 7

Figure 8A:
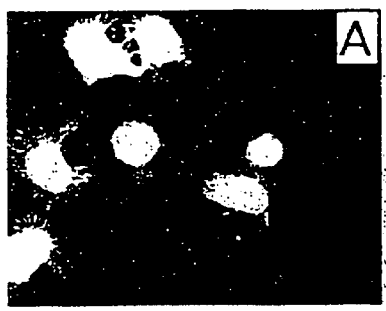
FIGS. 8A–8E show inhibition by pep2 of the spreading and redistribution of the actin cytoskeleton in IL-2- and PMA-activated FN-adherent T cells. T cells were activated (48 hr) with IL-2 (50 U/ml). The T cells were then washed and seeded onto FN-coated coverslips, in medium alone (8E), or in the presence of IL-2 (100 U/ml; 8A and 8C), PMA (50 ng/ml; 8B and 8D), or pep2 (10 pg/ml; 8C and 8D). After incubation, the intracellular actin filaments of the fixed FN-attached T cells were stained. Original magnification, =1000.
Figure 8B:
Figure 8C:
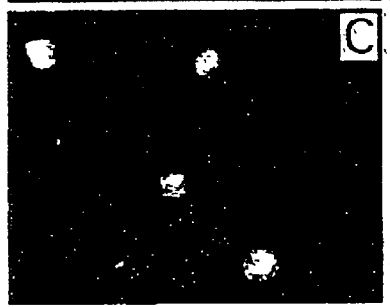
Figure 8D:
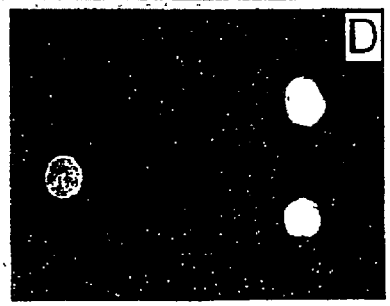
Figure 8E:
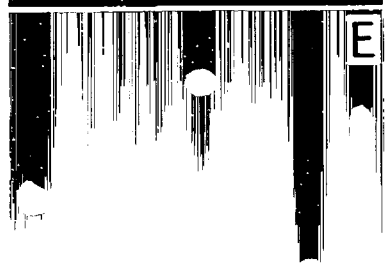

Inhibition of the reorganization of the actin cytoskeleton in FN-attached activated T cells by the Glu-Phe-Leu-Asn-Arg-Trp-Ile-Thr (SEQ ID NO:1) peptide. The adhesion of immune cells to ECM is dependent on the sequestering of the cytoplasmic domains of integrins in focal adhesion sites, together with actin-containing microfilament bundles (Sanchez-Mateos et al., 1996). Therefore, we examined the effect of Glu-Phe-Leu-Asn-Arg-Trp-Ile-Thr (SEQ ID NO:1) on the morphologies of adherent T cells. The T cells were activated with L-2 or PMA, treated with the IL-2 peptides, and seeded onto FN-coated coverslips. After incubation and fixation, the actin cytoskeleton of attached T cells was stained with TRITC-conjugated phalloidin. The morphologies of FN-bound IL-2- and PMA-activated T cells (FIGS. 8A, 8B) were markedly different from those of non-activated lymphocytes (FIG. 8E); the activated T cells appeared spread, and their actin cytoskeleton performed distinct structures typical of ECM-adherent cells. The Glu-Phe-Leu-Asn-Arg-Trp-Ile-Thr (SEQ ID NO:1) peptide inhibited the redistribution of the actin skeleton in both the IL-2- (FIG. 8C) and PMA-treated (FIG. 8D) FN-adherent T cells. Control peptides (reverse sequences of each peptide pep1, pep2, pep3) did not inhibit the actin reorganization of the activated T cells (not shown). Hence, the adhesion-inhibiting activity of the IL-2-derived peptide Glu-Phe-Leu-Asn-Arg-Trp-Ile-Thr (SEQ ID NO:1), similar to the Ile-Val-Leu peptide (data not shown), appears to involve inhibition of the redistribution of the actin cytoskeleton, and therefore, changes in cell shape and spreading.

Example 8

The effect of synthetic IL-2 derived peptides and derivatives thereof on spontaneous cytokine (IL-8) secretion from intestinal epithelial cells. Human colonic epithelial cell lines, such as HT-29, have been shown to secrete pro-inflammatory cytokines such as IL-1β and IL-8, in response to cytokines such as TNF-α, IL-1β, IFN-γ, and to LPS (Ecknamm et al., 1993), or as a response to bacterial invasion (Jung et al., 1995).

The effect of the synthetic IL-2 peptides pep1, pep2, pep3, and other synthetic derivatives of the sequences shown in Table 1 below, was tested on spontaneous IL-8 secretion from HT-29 cells as follows: HT-29 cells ($10^6$ cells/well) were seeded and incubated in culture medium for 24 h at 37° C. in 24-well plates with the desired peptide (1 nM), the supernatants were collected and IL-8 levels were determined by an ELISA assay, using Pharmingen antibody pairs, according to the manufacturer's instructions. The results in Table 1 show the O.D. readings of the ELISA assay (at 405 nm) as well as the percentage of inhibition of IL-8 secretion. A level of inhibition of about 30% or higher indicates that the peptide has relevant anti-inflammatory activity. These results show that the peptides inhibit the spontaneous secretion of IL-8 from a human colonic epithelial cell line and are, therefore, good candidates for the treatment of inflammatory, particularly, bowel diseases.

TABLE 1

Inhibitory effect of pep1, pep2, pep3 and analogues thereof on spontaneous IL-8 secretion from intestinal epithelial cells

| Peptide | Average O.D. | % inhibition |
|---|---|---|
| Background | 71 ± 1.4 | |
| Medium alone | 488 ± 8.5 | 0 |
| (pep1) Ile-Val-Leu, | 54 ± 19.1 | 104 |
| (pep4) Asn-Ile-Asn-Val-Ile-Val-Leu (SEQIDNO:3), | 34 ± 3.5 | 109 |
| (pep5) Ile-Val-Leu-Glu-Leu-Lys-Gly (SEQIDNO:4), | 35 ± 0.7 | 109 |
| (pep6) Asn-Val-Ile-Val-Leu (SEQIDNO:5) | 100 ± 14.8 | 93 |
| (pep7) Ala-Val-Leu | 170 ± 8.5 | 76 |
| (pep8) Ile-Ala-Leu | 35 ± 4.9 | 109 |
| (pep9) Ile-Val-Ala | 100 ± 9.9 | 93 |
| (pep10) Glu-Val-Leu | 125 ± 19.1 | 87 |
| (pep2) Glu-Phe-Leu-Asn-Arg-Trp-Ile-Thr (SEQIDNO:1) | 36 ± 4.2 | 108 |
| (pep15) Ile-Val-Glu-Phe-Leu-Asn-Arg-Trp-Ile-Thr (SEQIDNO:8) | 33 ± 0.7 | 109 |
| (pep16) Glu-Phe-Leu-Asn-Arg-Trp-Ile-Thr-Phe-Cys (SEQIDNO:9) | 126 ± 7.1 | 87 |
| (pep17) Ala-Thr-Ile-Val-Glu-Phe-Leu-Asn-Arg-Trp-Ile-Thr (SEQIDNO:10) | 150 ± 6.4 | 81 |
| (pep18) Glu-Phe-Leu-Asn-Arg-Trp-Ile-Thr-Phe-Cys-Gln-Ser (SEQIDNO:11) | 162 ± 12.0 | 78 |
| (pep19) Leu-Asn-Arg-Trp-Ile-Thr (SEQIDNO:12) | 152 ± 30.4 | 81 |
| (pep20) Arg-Trp-Ile-Thr (SEQIDNO:13) | 191 ± 4.9 | 71 |
| (pep21) Glu-Phe-Leu-Asn (SEQIDNO:14) | 195 ± 14.1 | 70 |
| (pep22) Ala-Phe-Leu-Asn-Arg-Trp-Ile-Thr (SEQIDNO:15) | 158 ± 4.2 | 79 |
| (pep23) Lys-Phe-Leu-Asn-Arg-Trp-Ile-Thr (SEQIDNO:16) | 36 ± 14.1 | 108 |
| (pep24) Glu-Ala-Leu-Asn-Arg-Trp-Ile-Thr (SEQIDNO:17) | 187 ± 16.3 | 72 |
| (pep25) Glu-Val-Leu-Asn-Arg-Trp-Ile-Thr (SEQIDNO:18) | 172 ± 2.8 | 76 |
| (pep26) Glu-Phe-Ala-Asn-Arg-Trp-Ile-Thr (SEQIDNO:19) | 156 ± 27.6 | 80 |
| (pep27) Glu-Phe-Leu-Ala-Arg-Trp-Ile-Thr (SEQIDNO:20) | 309 ± 18.4 | 43 |
| (pep28) Glu-Phe-Leu-Asn-Ala-Trp-Ile-Thr (SEQIDNO:21) | 120 ± 8.5 | 88 |
| (pep29) Glu-Phe-Leu-Asn-Glu-Trp-Ile-Thr (SEQIDNO:22) | 139 ± 19.8 | 84 |
| (pep30) Glu-Phe-Leu-Asn-Arg-Ala-Ile-Thr (SEQIDNO:23) | 123 ± 9.2 | 88 |
| (pep31) Glu-Phe-Leu-Asn-Arg-Trp-Ala-Thr (SEQIDNO:24) | 112 ± 18.4 | 90 |
| (pep32) Glu-Phe-Leu-Asn-Arg-Trp-Ile-Ala (SEQIDNO:25) | 80 ± 24.0 | 98 |
| (pep33) Glu-Phe-Leu-Asn-Arg-Trp-Ile-Thr-NH$_2$ (SEQIDNO:26) | 73 ± 5.7 | 100 |
| (pep3) Arg-Met-Leu-Thr (SEQIDNO:2) | 44 ± 0.7 | 107 |
| (pep36) Ala-Met-Leu-Thr (SEQIDNO:28) | 201 ± 17.7 | 69 |
| (pep37) Arg-Ala-Leu-Thr (SEQIDNO:29) | 222 ± 24.0 | 64 |
| (pep38) Arg-Met-Ala-Thr (SEQIDNO:30) | 157 ± 1.4 | 79 |
| (pep39) Arg-Met-Leu-Ala (SEQIDNO:31) | 160 ± 21.9 | 79 |
| (pep40) Lys-Met-Leu-Thr (SEQIDNO:32) | 179 ± 17.7 | 74 |
| (pep41) Arg-Val-Leu-Thr (SEQIDNO:33) | 132 ± 17.0 | 85 |
| (pep42) Arg-Met-Leu-Thr-NH$_2$ (SEQIDNO:34) | 226 ± 28.3 | 63 |
| (pep43) Pro-Lys-Leu-Thr-Arg-Met-Leu-Thr (SEQIDNO:35) | 57 ± 12.7 | 103 |
| (pep44) Arg-Met-Leu-Thr-Phe-Lys-Phe-Tyr (SEQIDNO:36) | 307 ± 29.7 | 43 |

The effect of the peptides was also tested on the TNF-α induced secretion of IL-1β from intestinal epithelial cells. Test cells (HT-29 or Caco-2) were grown as confluent monolayers in 24-well tissue culture plates. After the cells reached confluence, the culture medium was changed and the cells ($10^6$ cells/well) were incubated for 24 h at 37° C. with the IL-2 peptides (or control and derivative peptides) in 24-well plates with the addition of TNF-α. The peptides were added to the cells 1 hour prior to the addition of TNF-α. Following culture, the supernatants were harvested and analyzed for IL-1β secretion by ELISA using a commercially available kit (Genzyme), according to the manufacturers' protocols. The results are similar to those obtained above, the peptides being shown to inhibit TNF-α induced secretion of IL-1β in similar levels as above (data not shown).

REFERENCES

1. Baugh, J. and Travis, J. 1976. Human leukocyte granule elastase: rapid isolation and characterization. Biochemistry 15:836.
2. Ben-Baruch, A., M. Grimm, K. Bengali, G. A. Evans, O. Chertov, J. M. Wang, O. M. Howard, N. Mukaid, K. Matsushima, and J. J. Oppenheim. 1997. The differential ability of IL-8 and neutrophil-activating peptide-2 to induce attenuation of chemotaxis is mediated by their divergent capabilities to phosphorylate CXCR2 (IL-8 receptor B). J. Immunol. 158:5927.
3. Butcher, E. C. and L. J. Picker. 1996. Lymphocyte homing and homeostasis. Science 272:60.
4. Doring, G., F. Frank, C. Boudir, S. Herbert, B. Fleischer, and G. Bellon. 1995. Cleavage of lymphocyte surface antigens CD2, CD4, and CD8 by polymorphonuclear leukocyte elastase and cathepsin G in patients with cystic fibrosis. J. Immunol. 154:4842.
5. Ecknamm, L., Jung, H. C., Schurer Maly, C., Panja, A., Morzycka Wroblewska, E. and Kagnoff, M. F., Differential cytokine expression by human intestinal epithelial cell lines: regulated expression of interleukin 8 [comment], Gastroenterology, 105 (1993) 1689–97.
6. Gilat, D., L. Cahalon, R. Hershkoviz, and O. Lider. 1996. Counter-interactions between tissue-infiltrating T lymphocytes, pro-inflammatory mediators, and enzymatically modified extracellular matrix. Immunol. Today 17:16.
7. Jung, H. C., Eckmann, L., Yang, S. K., Panja, A., Fierer, J., Morzycka Wroblewska, E. and Kagnoff, M. F., A distinct array of proinflammatory cytokines is expressed in human colon epithelial cells in response to bacterial invasion, J-Clin-Invest, 95 (1995) 55–65.
8. Kuo, L. M. and R. J. Robb. 1986. Structure-function relationships for the IL 2-receptor system. II. Localization of an IL-2 binding site on high and low affinity receptors. J. Immunol. 137:1538.
9. Leppert, D., E. Waubant, R. Galardy, N. W. Bunnett, and S. L. Hauser. 1995. T cell gelatinases mediate basement membrane transemigration in vitro. J. Immunol. 154:4379.
10. Li, J., S. Gyorffy, S. Lee, and C. S. Kwok. 1996. Effect of recombinant human interleukin-2 on neutrophil adherence to endothelial cells in vitro. Inflammation 20:361.
11. Loetscher, P., M. Seitz, M. Baggiolini, and B. Moser. 1996. Interleukin-2 regulates CC chemokine receptor expression and chemotactic responsiveness in T lymphocytes. J. Exp. Med. 184:569.
12. Otey, C. A., F. M. Pavalko, and K. Burridge. 1990. An interaction between α-actinin and the $β_1$ integrin subunit in vitro. J. Cell. Biol. 111:721.
13. Packard, B. Z., H. S. Mostowski, and A. Komoriya. 1995. Mitogenic stimulation of human lymphocytes mediated by a cell surface elastase. Biochem. Biophys. Acta 1269:51.
14. Sanchez-Mateos, P., C. Cabaas, and F. Sanchez-Madrid. 1996. Regulation of integrin function. Sem. Cancer Biol. 7:99.
15. Taniguchi, T. and Y. Minami. 1993. The IL-2/IL-2 receptor system: a current overview. Cell 73:5.
16. Yavin, E. J., L. Yan, D. M. Desiderio, and M. Fridkin. 1996. Synthetic peptides derived from the sequence of human C reactive protein inhibit the enzymatic activity of human leukocyte elastase and cathepsin G. Int. J. Pep. Prot. Res. 48:465.

What is claimed is:

1. A synthetic anti-inflammatory peptide of IL-2 or an anti-inflammatory derivative thereof, which inhibits in vitro: (i) adhesion of activated T cells to fibronectin, laminin and/or collagen-type IV; (ii) chemotactic migration of T cells through fibronectin; and/or (iii) spontaneous or TNF-α-induced secretion of IL-8 or IL-1β, from intestinal epithelial cells, selected from the group consisting of:
   (i) peptides pep1, pep2, and pep3 consisting of the sequences:
      (pep1) Ile-Val-Leu
      (pep2) Glu-Phe-Leu-Asn-Arg-Trp-Ile-Thr (SEQ ID NO:1)
      (pep3) Arg-Met-Leu-Thr (SEQ ID NO:2)
   (ii) peptides obtained from pep2 by deletion of one or more amino acid residues;
   (iii) peptides obtained by addition to peptides (i) or (ii) of one or more natural or non-natural amino acid residues to the N-terminus and/or C-terminus;
   (iv) peptides obtained by replacement of one amino acid residue of peptides (i) to (iii) by another natural amino acid residue or by a non-natural amino acid residue;
   (v) peptides of (i) to (iii) which are all-L, all-D or a combination of D- and L-amino acid residues;
   (vi) amide derivatives of the C-terminal residue of peptides (i) to (v);
   (vii) cyclic derivatives of peptides (i) to (vi) in which the peptide is cyclized by an intramolecular bond; and
   (viii) dual peptides consisting of two of the same or combination of peptides (i) to (vii), wherein the two peptides are covalently linked to one another directly or through a spacer.

2. The synthetic peptide Ile-Val-Leu (pep1) and derivatives thereof according to claim 1, obtained by:
   (a) elongation by up to 3–4 further amino acid residues at the N- and/or C-terminal;
   (b) substitution of the Ile residue by a natural or non-natural amino acid hydrophilic polar neutral or negatively charged, or hydrophobic non-polar neutral amino acid residue;
   (c) substitution of the Val residue by a hydrophobic, non-charged natural or non-natural amino acid residue;
   (d) substitution of the Leu residue by a hydrophobic, non-charged natural or non-natural amino acid residue;
   (e) amidation of the C-terminal Leu residue;
   (f) cyclization of pep1 or of any peptide of (a) to (e); or
   (g) any combination of (a) to (f).

3. A synthetic peptide according to claim 2, selected from the group consisting of:
   (pep1) Ile-Val-Leu
   (pep4) Asn-Ile-Asn-Val-Ile-Val-Leu (SEQ ID NO:3),
   (pep5) Ile-Val-Leu-Glu-Leu-Lys-Gly (SEQ ID NO:4),
   (pep6) Asn-Val-Ile-Val-Leu (SEQ ID NO:5)
   (pep7) Ala-Val-Leu
   (pep8) Ile-Ala-Leu
   (pep9) Ile-Val-Ala
   (pep10) Glu-Val-Leu
   (pep11, linear) and (pep12, cyclic) Cys-Ile-Val-Leu-Ala-Cys (SEQ ID NO:6) and,
   (pep13, linear) and (pep14, cyclic) Cys-Ile-Val-Leu-Ala-Ala-Cys (SEQ ID NO:7).

4. The synthetic peptide Glu-Phe-Leu-Asn-Arg-Trp-Ile-Thr (SEQ ID NO:1) (pep2), and derivatives thereof according to claim 1, obtained by:
   (a) elongation at the C- and/or N-terminal ends by up to 4 further amino acid residues total;
   (b) substitution of the Glu residue by a natural or non-natural charged or polar charged amino acid residue (c) substitution of the Phe residue by a natural or non-natural hydrophobic aliphatic or aromatic amino acid residue;
   (d) substitution of the Leu residue by a natural or non-natural hydrophobic aliphatic or aromatic amino acid residue;
   (e) substitution of the Asn residue by a hydrophilic, non-charged, aliphatic natural or non-natural amino acid residue;
   (f) substitution of the Arg residue by a positively charged, natural or non-natural amino acid residue;
   (g) substitution of the Trp residue by a natural or non-natural hydrophobic, aliphatic or aromatic, amino acid residue;
   (h) substitution of the Ile residue by a natural or non-natural hydrophobic, aliphatic or aromatic, amino acid residue;
   (i) substitution of the Thr residue by an aliphatic hydrophobic amino acid residue or a hydroxy- or thio-containing amino acid residue;

(j) truncation by up to 4 amino acid residues from either the C or N terminal;

(k) amidation of the C-terminal Thr;

(l) cyclization of pep2 or of any peptide of (a) to (k); or (m) any combination of (a) to (l).

5. A peptide according to claim 4, selected from the group consisting of:

(pep2) Glu-Phe-Leu-Asn-Arg-Trp-Ile-Thr (SEQ ID NO:1)

(pep15) Ile-Val-Glu-Phe-Leu-Asn-Arg-Trp-Ile-Thr (SEQ ID NO:8)

(pep16) Glu-Phe-Leu-Asn-Arg-Trp-Ile-Thr-Phe-Cys (SEQ ID NO:9)

(pep17) Ala-Thr-Ile-Val-Glu-Phe-Leu-Asn-Arg-Trp-Ile-Thr (SEQ ID NO:10)

(pep18) Glu-Phe-Leu-Asn-Arg-Trp-Ile-Thr-Phe-Cys-Gln-Ser (SEQ ID NO:11)

(pep19) Leu-Asn-Arg-Trp-Ile-Thr (SEQ ID NO:12)

(pep20) Arg-Trp-Ile-Thr (SEQ ID NO:13)

(pep21) Glu-Phe-Leu-Asn (SEQ ID NO:14)

(pep22) Ala-Phe-Leu-Asn-Arg-Trp-Ile-Thr (SEQ ID NO:15)

(pep23) Lys-Phe-Leu-Asn-Arg-Trp-Ile-Thr (SEQ ID NO:16)

(pep24) Glu-Ala-Leu-Asn-Arg-Trp-Ile-Thr (SEQ ID NO:17)

(pep25) Glu-Val-Leu-Asn-Arg-Trp-Ile-Thr (SEQ ID NO:18)

(pep26) Glu-Phe-Ala-Asn-Arg-Trp-Ile-Thr (SEQ ID NO:19)

(pep27) Glu-Phe-Leu-Ala-Arg-Trp-Ile-Thr (SEQ ID NO:20)

(pep28) Glu-Phe-Leu-Asn-Ala-Trp-Ile-Thr (SEQ ID NO:21)

(pep29) Glu-Phe-Leu-Asn-Glu-Trp-Ile-Thr (SEQ ID NO:22)

(pep30) Glu-Phe-Leu-Asn-Arg-Ala-Ile-Thr (SEQ ID NO:23)

(pep31) Glu-Phe-Leu-Asn-Arg-Trp-Ala-Thr (SEQ ID NO:24)

(pep32) Glu-Phe-Leu-Asn-Arg-Trp-Ile-Ala (SEQ ID NO:25)

(pep33) Glu-Phe-Leu-Asn-Arg-Trp-Ile-Thr-NH$_2$ (SEQ ID NO:26) and, (pep34, linear) and (pep35, cyclic) Cys-Glu-Phe-Leu-Asn-Arg-Trp-Ile-Thr-Ala-Cys (SEQ ID NO:27).

6. The synthetic peptide Arg-Met-Leu-Thr (SEQ ID NO:2) (pep3), and derivatives thereof according to claim 1, obtained by:

(a) elongation by up to 4 further amino acid residues at the C and/or N terminal end;

(b) substitution of the Arg residue by a natural or non-natural positively charged amino acid residue;

(c) substitution of the Met residue by a natural or non-natural hydrophobic, aliphatic or aromatic, amino acid residue;

(d) substitution of the Leu residue by a natural or non-natural hydrophobic, aliphatic or aromatic, amino acid residue;

(e) substitution of the Thr residue by an aliphatic hydrophobic amino acid residue or a hydroxy- or thio-containing amino acid residue;

(f) amidation of the C-terminal Thr residue;

(g) cyclization of pep3 or of any peptide of (a) to (f); or (h) any combination of (a) to (g).

7. A peptide according to claim 6, selected from the group consisting of:

(pep3) Arg-Met-Leu-Thr (SEQ ID NO:2)

(pep36) Ala-Met-Leu-Thr (SEQ ID NO:28)

(pep37) Arg-Ala-Leu-Thr (SEQ ID NO:29)

(pep38) Arg-Met-Ala-Thr (SEQ ID NO:30)

(pep39) Arg-Met-Leu-Ala (SEQ ID NO:31)

(pep40) Lys-Met-Leu-Thr (SEQ ID NO:32)

(pep41) Arg-Val-Leu-Thr (SEQ ID NO:33)

(pep42) Arg-Met-Leu-Thr-NH$_2$ (SEQ ID NO:34)

(pep43) Pro-Lys-Leu-Thr-Arg-Met-Leu-Thr (SEQ ID NO:35)

(pep44) Arg-Met-Leu-Thr-Phe-Lys-Phe-Tyr (SEQ ID NO:36) and, (pep45, linear) and (pep46, cyclic) Cys-Arg-Met-Leu-Thr-Ala-Cys (SEQ ID NO:37).

8. A pharmaceutical composition comprising at least one synthetic peptide or peptide derivative according to claim 1, and a pharmaceutically acceptable carrier.

9. A method for the treatment and/or alleviation of chronic inflammatory disorders comprising administering to a subject in need thereof an effective amount of an anti-inflammatory synthetic peptide according to claim 1.

10. The synthetic peptide of claim 1, which is pep2 (SEQ ID NO:1).

11. A pharmaceutical composition comprising the synthetic peptide of claim 10 and a pharmaceutically acceptable carrier.

12. A method for the treatment and/or alleviation of chronic inflammatory disorders comprising administering to a subject in need thereof an effective amount of an anti-inflammatory synthetic peptide according to claim 10.

13. The synthetic peptide and derivatives thereof according to claim 4, wherein:

said elongation is according to the natural sequence of IL-2;

said substitution of the Glu residue is selected from the group consisting of Lys, Arg, Asp, Gln, and Asn;

said substitution of the Phe residue is selected from the group consisting of Ala, Val, Ile, Leu, Tyr, Trp, Phe, Met, and Nle;

said substitution of the Leu residue is selected from the group consisting of Ala, Val, Ile, Leu, Tyr, Trp, Phe, Met, and Nle;

said substitution of the Asn residue is Gln;

said substitution of the Arg residue is selected from the group consisting of Lys, Orn, and homoArg;

said substitution of the Trp residue is selected from the group consisting of Tyr, Ile, Leu, Nle, Tic, Phe, 4-phenyl-Phe, and 4-methyl-Phe;

said substitution of the Ile residue is selected from the group consisting of Tyr, Phe, Leu, Nle, and Tic; and said substitution of the Thr residue is selected from the group consisting of Ala, Ile, Leu, Cys, and Ser.

14. The synthetic peptide and derivatives thereof according to claim 2, wherein:

said elongation is according to the natural sequence of IL-2;

said substitution of the Ile residue is selected from the group consisting of Glu, Asp, Asn, Gln, Ala, and Val;

said substitution of the Val residue is selected from the group consisting of Ala, Ile, Leu, Met, Nle, and Phe; and said substitution of the Leu residue is selected from the group consisting of Ala, Ile, Met, Nle, Phe, and Val.

15. The synthetic peptide and derivatives thereof according to claim 6, wherein:

said elongation is according to the natural sequence of IL-2;

said substitution of the Arg residue is selected from the group consisting of Lys, Orn, homoArg, and diaminobutyric acid;

said substitution of the Met residue is selected from the group consisting of Phe, Tyr, Ile, Leu, Nle, and Tic;

said substitution of the Leu residue is selected from the group consisting of Phe, Tyr, Nle, and Tic; and said substitution of the Thr residue is selected from the group consisting of Ala, Ile, Leu, Ser, and Cys.

* * * * *